United States Patent
Chaturvedi et al.

(10) Patent No.: US 9,750,910 B2
(45) Date of Patent: Sep. 5, 2017

(54) SYSTEMS FOR AUTOMATICALLY REMOVING FLUID FROM MULTIPLE REGIONS OF A RESPIRATORY TRACT

(71) Applicant: COEO LABS PRIVATE LIMITED, Sampangiramanagar, Bangalore (IN)

(72) Inventors: Jagdish Chaturvedi, Bangalore (IN); Nitesh Kumar Jangir, Sikar (IN); Nachiket Deval, Pune (IN); Ramakrishna Pappu, New Delhi (IN); Raghuveer Rao, Bangalore (IN); Mohammed Sajid Ali, Mysore (IN); Vimal Kishore Kakani, Hyderabad (IN)

(73) Assignee: COEO LABS PRIVATE LIMITED, Bangalore (IN)

( * ) Notice: Subject to any disclaimer, the term of this patent is extended or adjusted under 35 U.S.C. 154(b) by 0 days.

(21) Appl. No.: 14/826,114

(22) Filed: Aug. 13, 2015

(65) Prior Publication Data
US 2016/0045698 A1  Feb. 18, 2016

(30) Foreign Application Priority Data
Aug. 14, 2014  (IN) ............................ 3988/CHE/2014

(51) Int. Cl.
*A61M 16/04*  (2006.01)
*A61M 16/20*  (2006.01)
(Continued)

(52) U.S. Cl.
CPC .... *A61M 16/0463* (2013.01); *A61M 16/0479* (2014.02); *A61M 16/0486* (2014.02);
(Continued)

(58) Field of Classification Search
CPC .......... A61M 16/0003; A61M 16/0066; A61M 16/0463; A61M 16/0486; A61M 16/105;
(Continued)

(56) References Cited

U.S. PATENT DOCUMENTS 4,305,392 A   12/1981  Chester
4,584,998 A    4/1986  McGrail
(Continued)

FOREIGN PATENT DOCUMENTS

EP   2445562 A2   5/2012
EP   2552293 B1   2/2013
(Continued)

*Primary Examiner* — Quynh-Nhu H Vu
(74) *Attorney, Agent, or Firm* — Shay Glenn LLP

(57) ABSTRACT

Systems and devices for monitoring, detecting, and removing fluid build-up found at various regions along a tracheal tube of an intubated patient. The fluid management system includes pressure and flow sensors for detecting whether there is fluid at the various regions along the tracheal tube, and a means for drawing out the fluid into collection jars. The system also includes lavage features that is able to rinse different the various regions along a tracheal tube. Also disclosed are respiration insertion devices that either couple to existing tracheal tubes or incorporate tracheal tubing, where the respiration insertion body has channels and ports that contact various regions along the tracheal tube. The combination of the fluid management system and the respiration insertion devices effectively monitor and remove fluid at various locations along a tracheal tube of an intubated patient.

14 Claims, 33 Drawing Sheets

(51) Int. Cl.
*A61M 16/10* (2006.01)
*A61M 16/00* (2006.01)

(52) U.S. Cl.
CPC . *A61M 16/0465* (2013.01); *A61M 2205/3334* (2013.01); *A61M 2205/3344* (2013.01); *A61M 2205/3584* (2013.01); *A61M 2205/3592* (2013.01); *A61M 2205/505* (2013.01); *A61M 2205/75* (2013.01)

(58) Field of Classification Search
CPC ........ A61M 16/201; A61M 2016/0027; A61M 2016/003; A61M 2205/3334; A61M 2205/35; A61M 2205/50; A61M 2205/75
See application file for complete search history.

(56) References Cited

U.S. PATENT DOCUMENTS

| | | |
|---|---|---|
| 4,637,389 A | 1/1987 | Heyden |
| 4,840,173 A | 6/1989 | Porter |
| 4,865,586 A | 9/1989 | Hedberg |
| 5,143,062 A | 9/1992 | Peckham |
| 5,311,864 A | 5/1994 | Huerta |
| 5,582,167 A | 12/1996 | Joseph |
| 5,819,723 A * | 10/1998 | Joseph .............. A61M 16/0479 128/202.22 |
| 6,254,591 B1 | 7/2001 | Roberson |
| 6,460,540 B1 | 10/2002 | Klepper |
| 7,089,942 B1 | 8/2006 | Grey |
| 7,305,985 B2 | 12/2007 | Brain |
| 7,478,636 B2 | 1/2009 | Madsen et al. |
| 7,802,574 B2 | 9/2010 | Schultz |
| 8,042,544 B2 | 10/2011 | Ward et al. |
| 8,434,488 B2 | 5/2013 | Li et al. |
| 8,480,722 B2 | 7/2013 | Klepper |
| 8,707,956 B2 | 4/2014 | Blom et al. |
| 9,004,069 B2 | 4/2015 | Efrati et al. |
| 9,044,557 B2 | 6/2015 | Finneran et al. |
| 2002/0014238 A1 | 2/2002 | Kotmel |
| 2007/0028925 A1 | 2/2007 | Madsen et al. |
| 2007/0044807 A1 | 3/2007 | Madsen et al. |
| 2008/0121236 A1 | 5/2008 | Field |
| 2009/0038620 A1 | 2/2009 | Efrati |
| 2009/0142430 A1 | 6/2009 | Sanders et al. |
| 2009/0260632 A1 | 10/2009 | Abnousi et al. |
| 2010/0051035 A1 | 3/2010 | Jenkins et al. |
| 2010/0258134 A1 | 10/2010 | Colburn et al. |
| 2010/0307507 A1 | 12/2010 | Li et al. |
| 2012/0024293 A1 | 2/2012 | Maguire et al. |
| 2012/0097168 A1 | 4/2012 | Perez et al. |
| 2012/0180791 A1 | 7/2012 | Ciccone |
| 2013/0023729 A1 | 1/2013 | Vazales et al. |
| 2013/0030249 A1 | 1/2013 | Vazales et al. |
| 2013/0160771 A1 | 6/2013 | Suijs |
| 2013/0340748 A1 | 12/2013 | Alqudah |
| 2014/0000622 A1 | 1/2014 | Azagury et al. |
| 2014/0096766 A1 | 4/2014 | Avitsian et al. |
| 2014/0135641 A1 | 5/2014 | Wachtell et al. |
| 2014/0366874 A1* | 12/2014 | Deutsch .............. A61M 16/044 128/202.13 |
| 2016/0030663 A1* | 2/2016 | Adaniya ................. A61M 5/20 604/28 |
| 2016/0030708 A1* | 2/2016 | Casiello ............ A61M 25/0043 604/218 |

FOREIGN PATENT DOCUMENTS

| | | |
|---|---|---|
| EP | 1960024 B1 | 2/2014 |
| EP | 2349423 B1 | 2/2014 |
| WO | WO99/38548 A2 | 8/1999 |
| WO | WO99/66975 A1 | 12/1999 |
| WO | WO2007/013064 A1 | 2/2007 |
| WO | WO2007/130579 A2 | 11/2007 |
| WO | WO2008/009947 A1 | 1/2008 |
| WO | WO2010/062603 A1 | 6/2010 |
| WO | WO2011/013015 A1 | 2/2011 |
| WO | WO2011/126812 A1 | 10/2011 |
| WO | WO2012/003067 A1 | 1/2012 |
| WO | WO2012/087822 A1 | 6/2012 |
| WO | WO2012/087837 A1 | 6/2012 |
| WO | WO2012/087839 A1 | 6/2012 |
| WO | WO2012/087841 A1 | 6/2012 |
| WO | WO2013/030821 A1 | 3/2013 |
| WO | WO2013/102905 A1 | 7/2013 |
| WO | WO2015/042607 A1 | 3/2015 |
| WO | WO2015/063459 A1 | 5/2015 |

* cited by examiner

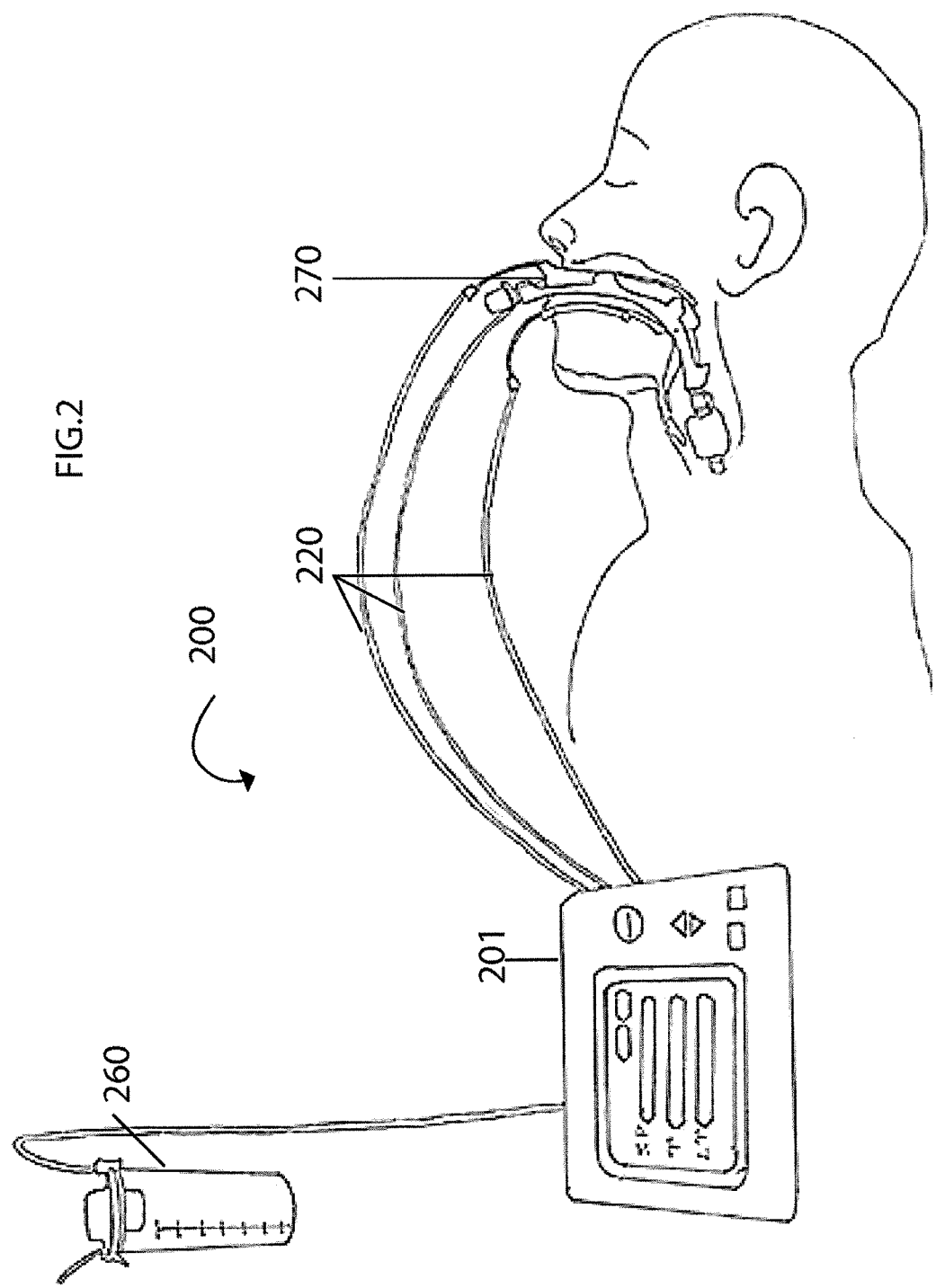

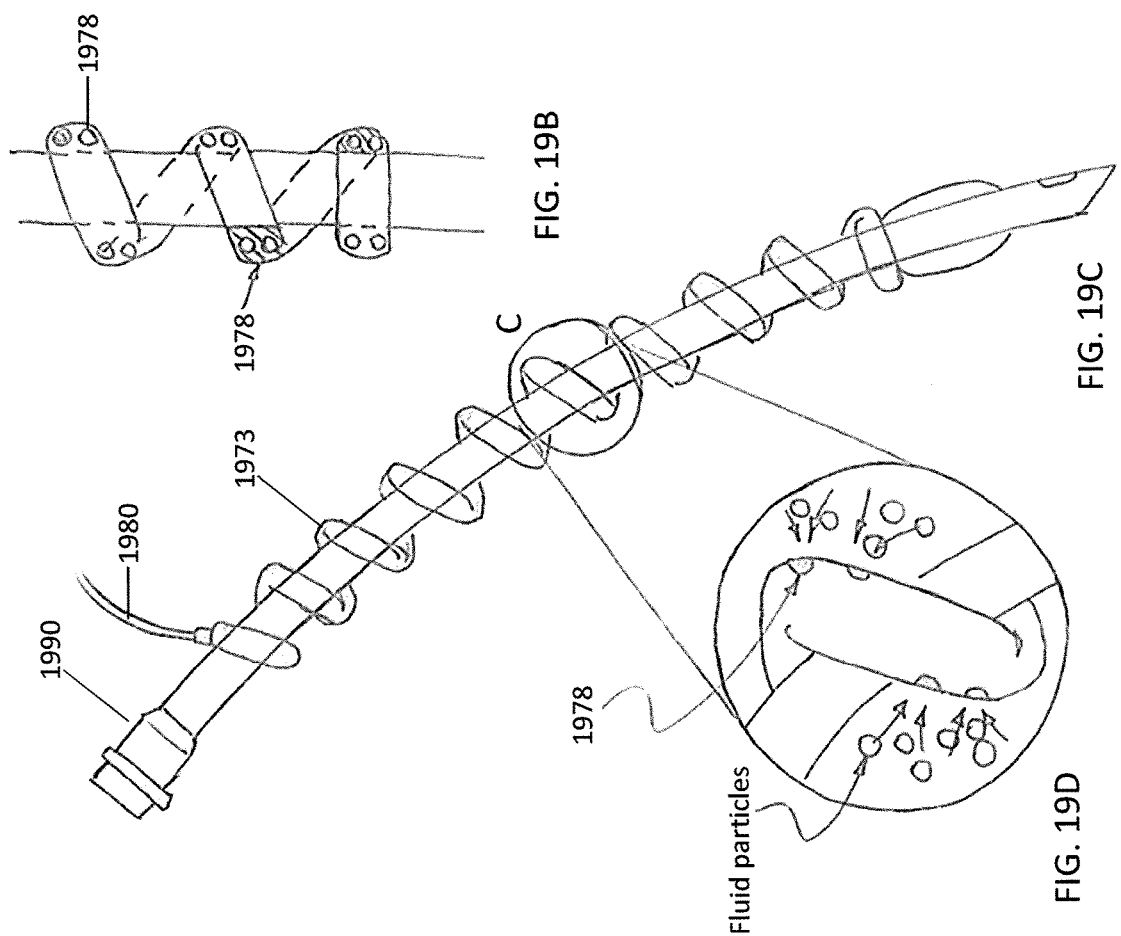

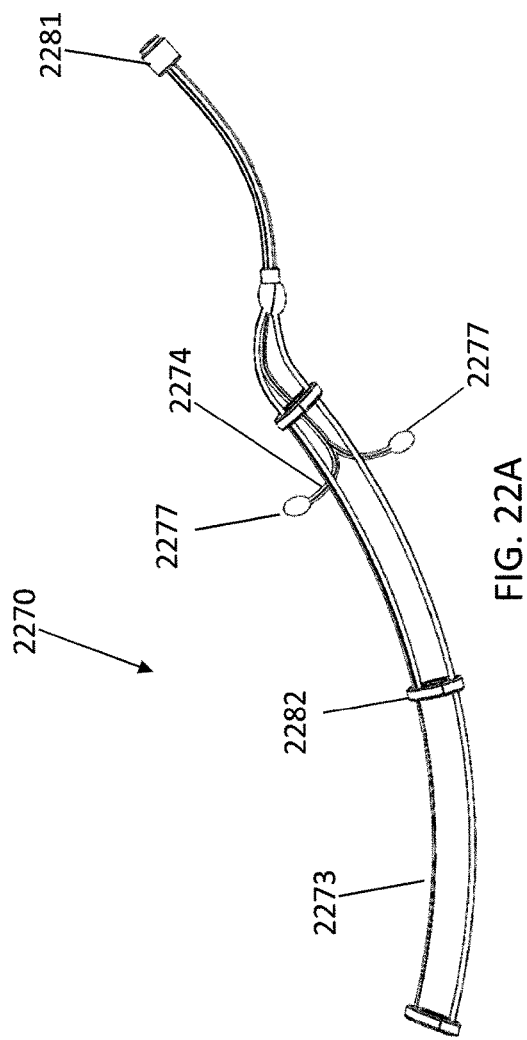
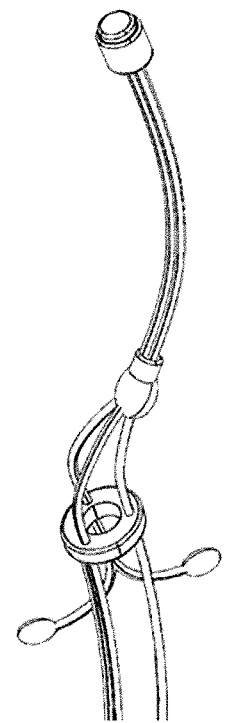
FIG. 22A
FIG. 22B
FIG. 22C

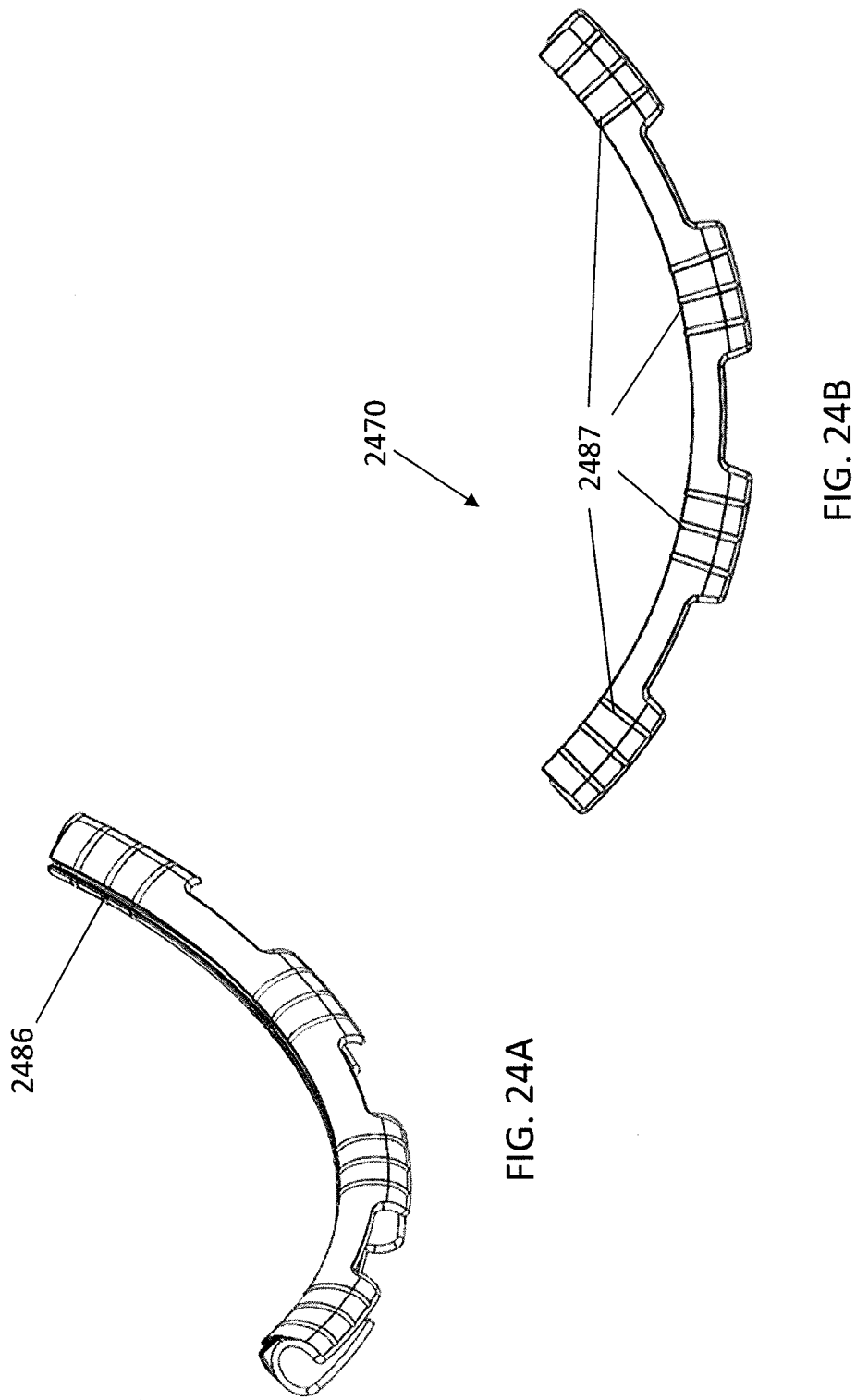

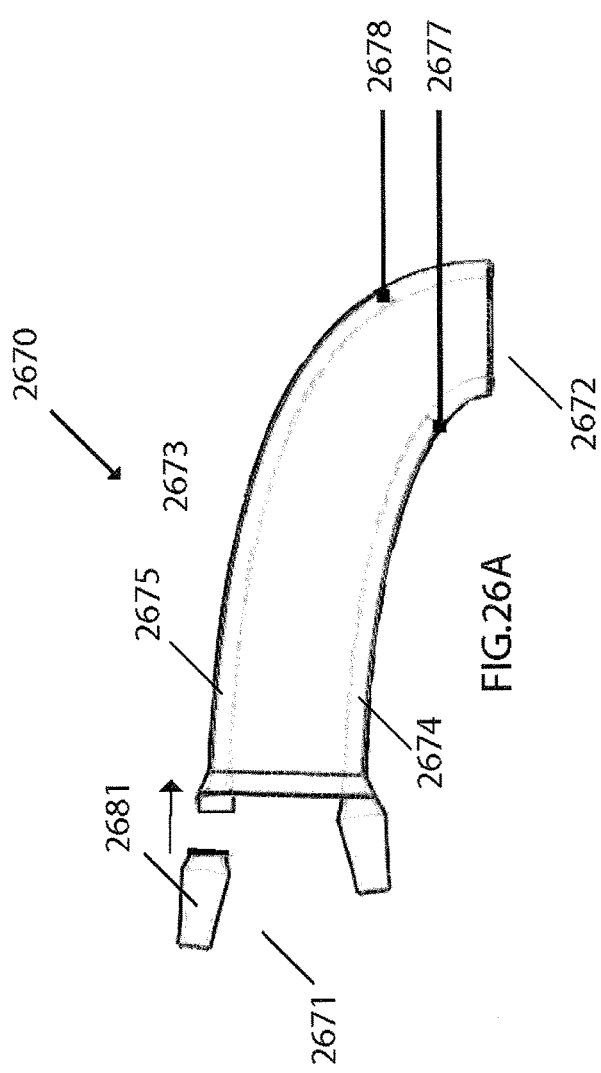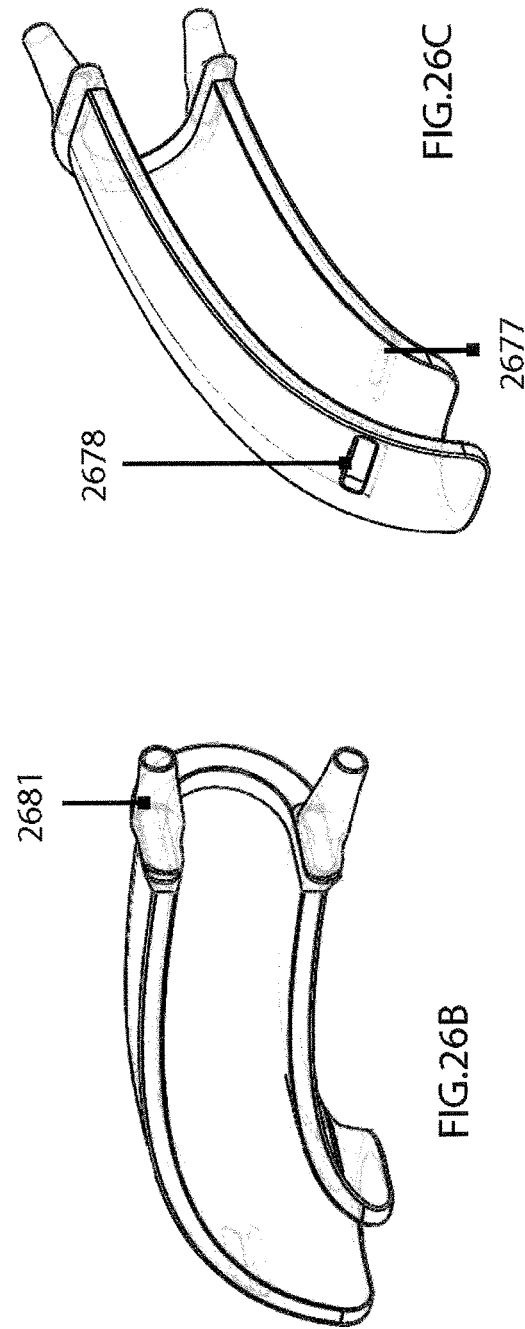
FIG.26A
FIG.26B
FIG.26C

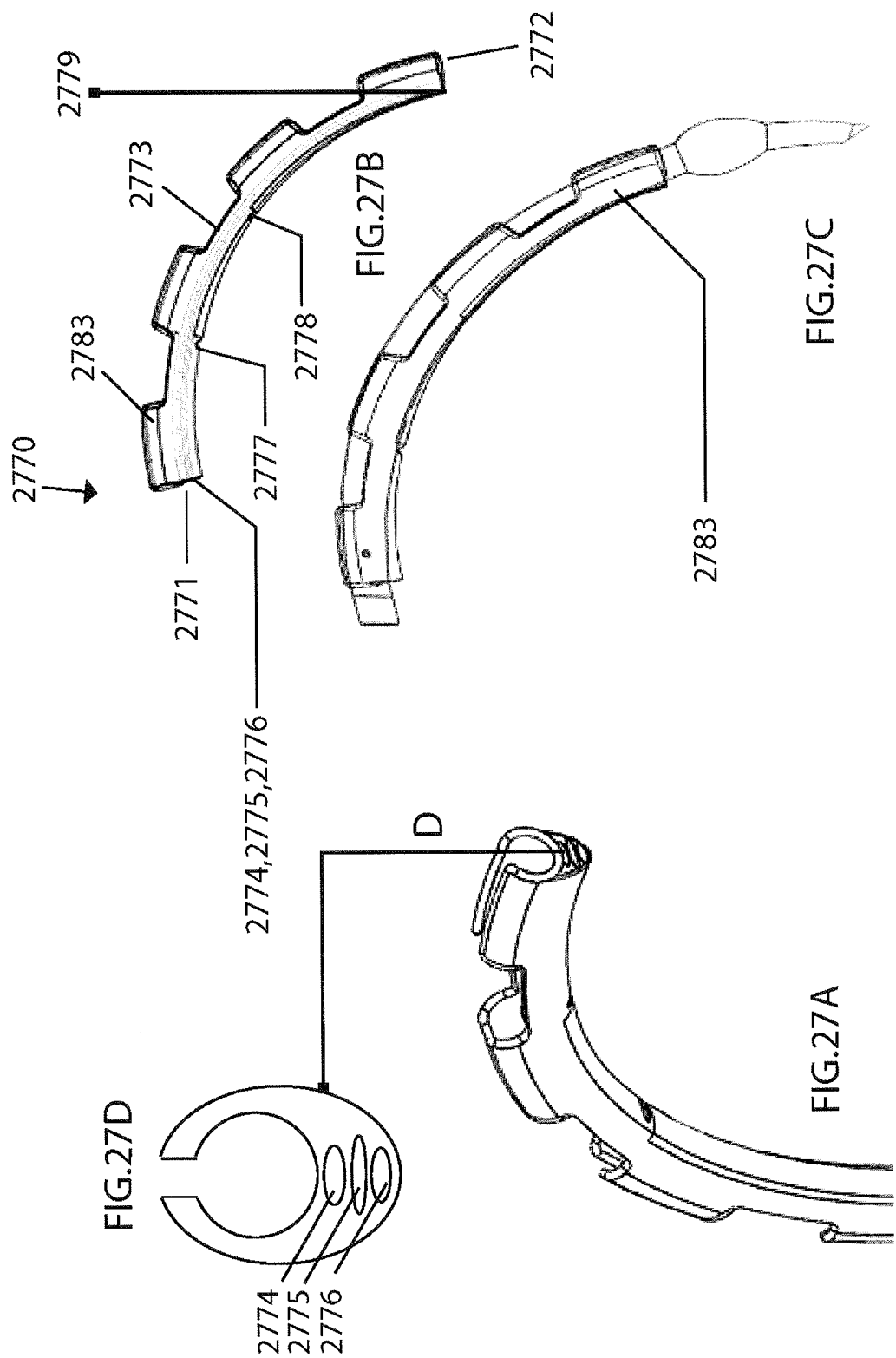

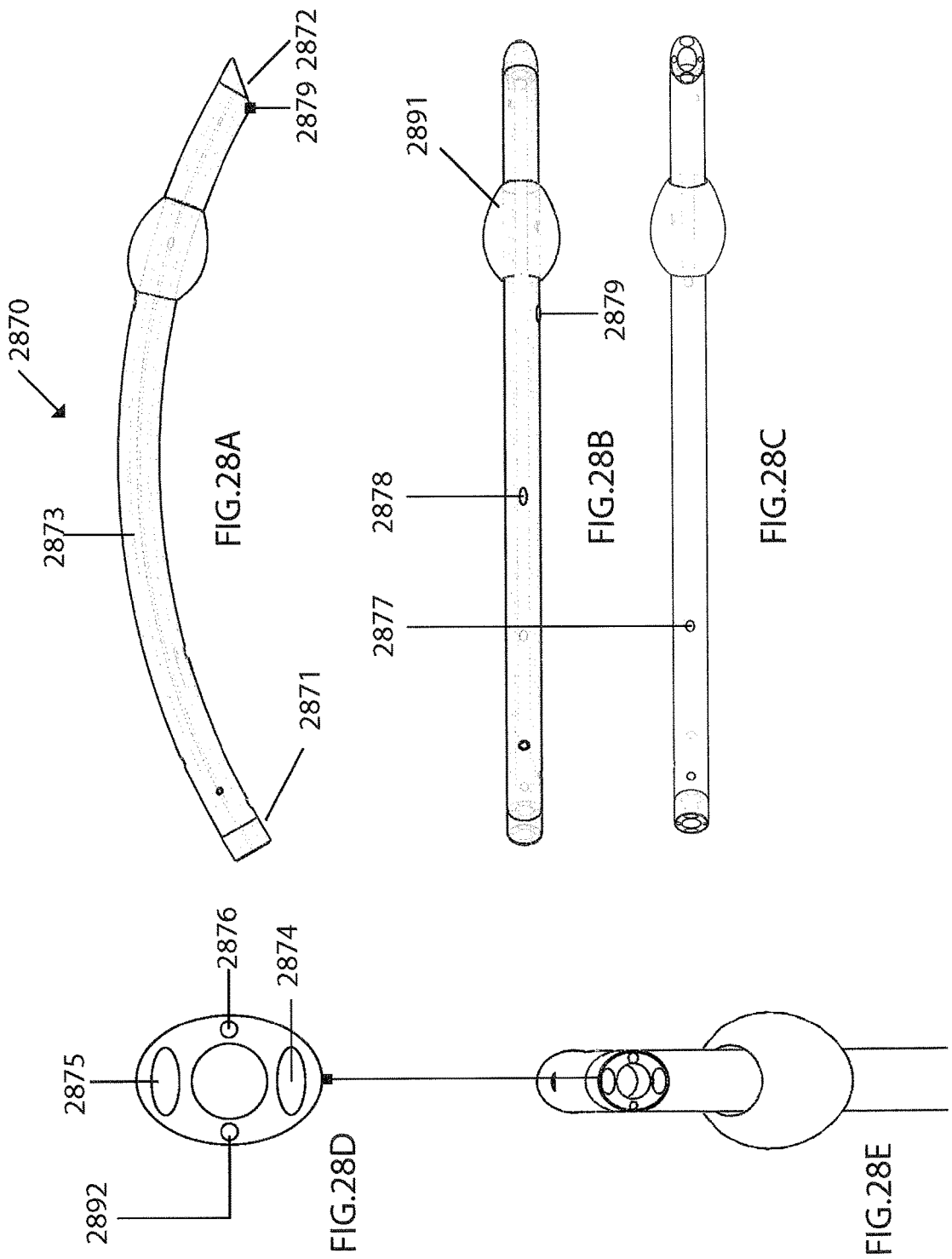

SYSTEMS FOR AUTOMATICALLY REMOVING FLUID FROM MULTIPLE REGIONS OF A RESPIRATORY TRACT

CROSS REFERENCE TO RELATED APPLICATION

This patent application claims priority to India Provisional Application No. 3988/CHE/2014, filed on Aug. 14, 2014, entitled "DEVICE AND METHOD FOR REMOVAL OF SECRETIONS TO PREVENT VENTILATOR ASSOCIATED PNEUMONIA", the disclosure of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure relates generally to fluid management apparatuses including or for use with tracheal tubes and related devices. More particularly, the disclosure relates to fluid management systems that are able remove secretions and monitor blockages from crucial points along an endotracheal tube either continuously or at predefined intervals. When a blockage is detected, the system is able to then clear the blockage. Fluids and mucous can then be collected for analysis. Devices are respiration insertion devices that monitor and remove fluid at different regions along a tracheal tube.

BACKGROUND

Tracheal tubes are inserted into the airway of patients in medical situations where the patient is unable to breathe on his own due to obstructions or lack of awareness/consciousness on the patient's part. Tracheal tubes aid in mechanically ventilating patients until the patients are able to breathe on their own. Most tracheal tubes currently in use include an inflatable cuff or balloon between the tracheal tube and the walls of the patient's trachea. The balloon or cuff blocks off the airway passage and establishes a closed system where gas pressure to the patient's lungs can be more easily regulated and the cuff or balloon helps to prevent passage of fluids and debris into the patient's trachea. FIGS. 1A-1B show typical respiratory tract locations where fluid might build in an intubated patient. While FIG. 1A shows that primary fluid accumulation typically occurs above an inflatable cuff of a tracheal tube, FIG. 1B shows that other regions along the trachea of an intubated patient may also be susceptible to fluid accumulation.

A major complication associated with intubation and the use of tracheal tubes is ventilator-associated pneumonia (VAP). VAP is a type of lung infection that occurs in patients who are placed on ventilators. VAP typically affects those who are already weak, such as patients in an intensive care unit (ICU) and/or with compromised immune systems. Developing VAP can increase the length of time a patient is in the ICU and the hospital. VAP also increases the likelihood of death by 20-30%.

VAP generally occurs because the tracheal tube allows passage of bacteria into the lower portions of the lung in an intubated patient. These patients may already have underlying issues that decrease their resistance to bacteria. Bacteria may thrive in the fluid accumulated around the tracheal tube, especially where there are bends in the tracheal tube which allow fluid to accumulate. Thus the initial bend in the tracheal tube between the back of the oral cavity and just past the pharynx, as well as the area above the inflatable cuff or balloon, may be especially prone to fluid and mucous accumulation. When patients remain on a ventilator for extended periods, the risk of bacterial infection increases. Further, bacteria also may be drawn down towards the lung when breathing. In addition, the bacteria that cause VAP can be differentiated from bacteria that cause the more common community-acquired pneumonia (CAP). Several bacteria associated with VAP are resistant to commonly-used antibiotics. Thus it would be desirable to minimize the amount of fluid collecting along the tracheal tube that can provide a hospitable media for bacteria to grow.

Existing mechanism for addressing the fluid build-up around a tracheal tube are not adequate. In the majority of currently available and described systems, the apparatus is only designed to draw fluid away from the tracheal tube at one location or if there is potential for more than one location of suction along the tracheal tube, the additional area is limited to the region immediately above the inflated cuff or balloon. In some variations ports are disposed along a tracheal tube at two locations, but these locations are not associated with specific anatomical locations on a patient. For example, U.S. Pat. No. 8,434,488 ('488) describes a tracheal tube with multiple ports that are integrated with the main tracheal tube opening. The tracheal tube in '488 includes only one suction lumen where the suctioning occurs in slightly distal to the cuff. The '488 tracheal tube also includes a line for inflating the cuff and maintaining a certain pressure within the cuff. FIGS. 1C and D shows traditional fluid management systems where suction only occurs at the region directly above the inflatable cuff. In addition, traditional fluid management systems require the caregiver to manually suction out any fluid present throughout the course of time that a patient is intubated, which requires more staff time of an already short-staffed health system.

Thus, there exists a need for fluid management apparatuses for use with ventilation that can monitor for fluid accumulation along different regions of a respiratory (e.g., tracheal) insert and automatically and periodically remove fluid.

SUMMARY OF THE DISCLOSURE

The present invention relates to apparatus (including systems and devices) and methods for periodically (and automatically) removing fluid accumulation at three or more regions along a respiratory insertion device (e.g., tube) that are most likely to collect fluid, so that any accumulated fluid may be removed. These apparatuses may also be configured to flush the fluid lines and/or provide a lavage to the patient.

Certain regions (corresponding to the patient's anatomy) along a respiratory insertion device (such as an endotracheal tube, tracheostomy tubes etc., which may be referred to herein for convenience as a "tracheal tube") are more prone to fluid collection when inserted into a patient in a 30 degree reclined/horizontal position. Three identified regions include the subglottic region directly above the inflatable balloon or cuff, an oropharynx cavity located past the oral cavity, and in the oral cavity. Being able to remove fluid build-up in these three regions will significantly reduce the likelihood of VAP in an intubated patient.

The fluid management apparatuses described herein can automatically remove fluid from multiple regions of the respiratory tract of a patient. In some variations, the fluid management apparatus (e.g., system) can be manually set to remove fluid from different regions along a tracheal tube. Also discussed herein are respiratory insertion devices that may attach to the fluid management system, although the fluid management apparatuses described herein may also be configured to operate with existing commercially available respiratory insertion devices (e.g., endotracheal tubes and tracheostomy tubes).

A fluid management system may include an input (e.g., button, touchscreen, dial, switch, etc.) that is able to receive user selected control information such as lavage delivery frequency, lavage duration, lavage pressure, suction application frequency, and suction pressure. In some variations, the user can set the pressure threshold for determining whether there is a blockage within a fluid line connected to a respiratory insertion device. The thresholds may also be pre-set. For example, pre-set values may be set by the manufacturer. The threshold values for pressure may be the same for each of the separate lines, but different pressure values for different lines may be selected in some variations.

The fluid management apparatuses described herein may also have other control and sensing components. This may include suction valves that are in fluid communication with sensors and suctioning mechanism. Valves may control the flow of fluid within the fluid lines. These apparatuses may also include flow and pressure sensors that detect either or both the presence of fluid in a particular line, and/or blockage within the fluid lines as well as monitor when all the fluid has been removed from a particular region. The system may also include filters before and/or after the valves and sensors connected or connectable to one or more fluid lines. The filters may minimize contamination reaching the valves and sensors.

The apparatuses described herein may automatically remove fluid from multiple regions along a respiratory tract. The system may also be configured to lavage an oral cavity portion of the respiratory tract. In some variations, the system includes controller circuitry, a display, and one or more valves configured to couple to a source of air pressure. The system may also include a first, a second, and a third fluid line, wherein the first, second and third fluid lines couple with the one or more valves of the controller and wherein the controller is configured to independently apply positive or negative pressure through each of the first, second or third fluid lines. The first fluid line can couple to a first flow sensor and a first pressure sensor, the second fluid line can couple to a second flow sensor and a second pressure sensor, and third fluid line can couple to a third flow sensor and a third pressure sensor. The flow sensors can be outside of their respective fluid lines. In some variations there are 4 fluid lines, with an additional fluid line as well as the three (oral, oropharynx and subglottic) lines mentioned above. The additional fluid line may remove secretions from inside the respiratory insertion device (e.g., endotracheal tube) either by using a closed suction catheter or using a modified respiratory insertion device with an additional lumen at the distal end facing inwards to remove secretions from inside the respiratory insertion device (e.g., endotracheal tube).

The fluid management system's controller circuitry may be configured to periodically, automatically, and independently apply negative pressure to each of the first, second and third fluid lines (and in some variations additional fluid lines, such as a fourth, or tracheal, fluid line), and to stop applying negative pressure in the first, second or third fluid lines when fluid flow in the first, second or third fluid line is below a first flow threshold and when pressure in that fluid line is above a first pressure threshold. The controller circuitry may also apply positive pressure to the first, second or third fluid lines when the fluid flow is below the first flow threshold when applying negative pressure and the pressure is below a second pressure threshold in the first second or third fluid lines. Finally, the controller circuitry may be configured to display for one or more of the first, second and third fluid lines data comprising one or more of flow rate of a secretion within the fluid line, thickness of secretion within the fluid line, volume of secretion within the fluid line, or color of the secretion within the fluid line.

The fluid management system may also include a lavage system (or sub-system). The lavage system (sub-system) may apply positive pressure to deliver a lavage fluid through one of the fluid lines (e.g., the line connected to the region of the respiratory insertion device within the oral cavity) and to apply negative pressure to one or more other of the fluid lines to remove the lavage fluid. The pump may be in communication with the controller and the source of lavage fluid and can be signaled to provide positive pressure to the fluid lines. The system may include a plurality of fluid lines that directly connect (or they may be connected via separate one or more lavage delivery fluid lines) to the source of lavage liquid. The controller may signal the lavage pump to apply positive pressure to the one or more lavage delivery fluid lines to deliver lavage fluid. Any of these apparatuses may also include one or more receptacles for holding returned lavage fluid.

Thus, any of these systems may also include a source of lavage fluid (e.g., antibacterial mouthwash, etc.), where the controller is configured to automatically apply positive pressure to deliver lavage liquid at a lavage delivery frequency; and a first collection container coupled to the first fluid lines to collect fluid from the first fluid line, a second collection container coupled to the second fluid line to collect fluid from the second fluid line, and a third collection container coupled to the third fluid line to collect fluid from the third fluid line.

As mentioned above, these apparatuses may also include an input configured to receive user-selected control information, which may include (or be limited to) control information regarding suction and/or lavage, including: lavage delivery frequency, lavage duration, lavage pressure, suction application frequency, suction duration, and suction pressure.

In general, any of these apparatuses may also include one or more filters, wherein one or more valves is in communication with fluid lines through the one or more filters. The valves may be suction valves, where a first suction valve is between the first fluid line and the source of air pressure, a second suction valve is between the second fluid line and the source of air pressure and a third suction valve is between the third fluid line and the source of air pressure.

As mentioned, the apparatus may also include one or more lavage delivery fluid lines that are connected to the source of lavage liquid and wherein the controller is configured to apply positive pressure to the one or more lavage delivery fluid lines to deliver lavage fluid. The apparatus may also include a pump configured to apply positive pressure, wherein the pump is in communication with the controller and the source of lavage fluid. Thus, the controller may be configured to apply positive pressure to deliver the lavage fluid through the first fluid line and to apply negative pressure to the first, second and third fluid lines to remove the lavage fluid. Finally the apparatus may include a vessel for collecting the used lavage fluid.

The fluid management systems described herein may also include an output, such as a display (e.g., screen, monitor, etc.), where data regarding the first, second, and in some variations, a third, fourth, or additional fluid lines are shown. Data can include flow rate of a secretion within the fluid line, thickness of secretion within the fluid line, volume of secretion within the fluid line, or color of the secretion within the fluid line.

Any of these apparatuses may include collection containers. One or more, e.g., a first, second and third (and in some variations a fourth) collection container, may be coupled to a first, second, and third fluid line, where each is connected to a valve of the one or more valves and the source of air pressure.

The respiratory insertion device extends distally along its major axis. The respiratory insertion device includes a first and a second lumen where the first and second lumen includes a first and a second opening in fluid connection with the first and the second lumen, respectively. The first and second opening are located spatially from each other along the tracheal tube such that two regions along the tracheal tube prone to fluid accumulation correspond to the location of the first and second opening. In some cases, the first and the second opening are at least 0.4 inch from each other. In other examples, a third lumen having a corresponding third opening is also disposed along the tracheal tube in a region away from and not in the regions corresponding to the location of the first and the second openings of the first and second lumen.

The first, the second, and potentially a third lumen all include a means for fluidly connecting to corresponding fluid lines at an opposite terminus from their respective openings. The fluid lines are coupled to a suctioning apparatus, such as a pump, that is able to draw fluid away from the regions associated with the first, second, and third openings. There may be separate fluid lines that connect to the first, the second, and the third lumen or there may be one fluid line that serves to remove fluid from all the lumen present using appropriate connectors.

The fluid management system also includes a controller that is in electrical communication with the sensors, the pump or pumps, valves and other components. The controller periodically will test for fluid or mucous blockage within the different lumen that correspond to the different regions of the tracheal tube. If blockage is detected the controller will communicate to the pump(s) to apply positive and then negative pressure to clear away the fluid and mucous.

In general, a tracheal tube is a catheter that is inserted into the trachea for the primary purpose of establishing and maintaining a patent airway and to ensure the adequate exchange of oxygen and carbon dioxide. Many different types of tracheal tubes are available, suited for different specific applications, including endotracheal tubes and tracheostomy tubes. For example, an endotracheal tube (ET) is typically a specific type of tracheal tube that is nearly always inserted through the mouth (orotracheal) or nose (nasotracheal). A tracheostomy tube is another type of tracheal tube, which may be, e.g., a 2-3-inch-long curved metal or plastic tube that may be inserted into a tracheostomy stoma (following a tracheotomy) to maintain a patent lumen. The respiratory (or in some variations, endorespiratory) insertion devices described herein may be tracheal tubes or they may be adapted for use with a tracheal tube, as described in greater detail below.

The system can couple to a respiratory insertion device (which may also be referred to as a respiratory insertion body), where the respiratory insertion device extending distally in an elongate axis, the respiratory insertion device may include a plurality of lumen extending in the elongate axis, and a plurality of openings, wherein each lumen is in fluid connection with an opening, and where the openings for different lumen are separated along the elongate axis by at least 0.4 inches. In general, each of the lumen in the plurality of lumen are configured to fluidly connect with one of the first, second or third fluid lines. As described in detail below, in some variations the systems described herein may include additional fluid lines, and in particular a fourth fluid line that is configured to attach to a lumen in a tracheal device that may be connected to remove fluid from within the central and/or main lumen of the tracheal tube. This may be referred to as a tracheal line.

As mentioned, the respiratory insertion devices described herein may be tracheal tubes or they may connect to an existing tracheal tube. In the former case where the tracheal tube incorporates the fluid management features, the respiratory insertion device may have three or more (e.g., 4) integrated lumens along with the main tracheal tube passageway, e.g., the three lumens for the locations already mentioned and a fourth lumen to remove secretions from inside the main tracheal tube. As previously mentioned, suction of pre-determined regions along the tracheal tube path is through openings along the respiratory insertion device. In the latter case, where the respiratory insertion device attaches to an existing endotracheal tube, several examples are described herein. In one example, the respiratory insertion device can clip onto an existing endotracheal tube and be slid down along the length of the tracheal tube. The respiratory insertion device clip includes separate lumen having corresponding openings that contact pre-determined regions along the tracheal tube. In some variations of the respiratory insertion device clip may have a hinge for easier placement of the respiratory insertion device.

The respiratory insertion body can independently remove fluid from multiple regions of a respiratory tract. The respiratory insertion body may have an elongate axis extending proximally to distally with a first lumen disposed along the elongated body having a first lumen proximal end and a first lumen distal end, a second lumen disposed along the elongated body having a second lumen proximal end and a second lumen distal end, and a third lumen disposed along the elongated body having a third lumen proximal end and a third lumen distal end. In some variations, the apparatus may include a first, second, and third opening disposed respectively on the first, second, and third lumen distal end. The first, second and third openings may be positioned along the elongate body so that the first, second and third openings are separated from each other by at least 0.4 inches along the elongate axis. The first opening in respiratory insertion body may be configured to be positioned in the oral cavity of a user, the second opening is configured to be positioned at a oropharynx region of the user, and a third opening through the endotracheal insertion body is configured to be positioned at a subglottic region of the user when the endotracheal insertion body is inserted into the user's throat. In some examples, the elongate body comprises a tubular body having a central tracheal tube lumen opening at a proximal end and a distal end of the endotracheal insertion body. In other examples, the elongate body comprises a sheath configured to connect over an endotracheal tube. The elongated body may also be a spiral sheath configured to connect over an endotracheal tube. In some cases, a series of clips/ attachments that can fit over an endotracheal tube. In general, the first lumen proximal end, the second lumen proximal end, and the third lumen proximal end each comprise a fluid line coupler configured to attach to a fluid line. Finally, first opening is between about 3 cm and 14 cm from the third opening, and further wherein the second opening is between about 2 cm and 10 cm from the third opening.

Some of the respiratory insertion devices described herein are for coupling to tracheostomy tubes or may incorporate a tracheostomy tube. In one case, the insertion device has a bifurcated elongate body having a first arm and a second arm, the body having an elongate axis extending proximally to distally. The first arm is configured to extend through a lumen of the tracheal tube and comprises a bent distal end region configured to extend out of a distal end of the tracheostomy tube, wrap around the distal end of the tracheal tube and extend proximally up the tracheal tube. The second arm is configured to extend distally along the outside of the tracheal tube. A first and second opening disposed within the first arm of the elongated body. The first opening is disposed proximal to the bent distal end region of the first arm and configured to reside within the lumen of the tracheal tube. The second opening may be disposed distally to the bent distal end region and configured to reside outside of a distal end region of the tracheal tube. A third opening may be disposed on a third lumen within the second arm, the third opening disposed near a distal end of the second arm. The proximal end of the first lumen may comprise a first fluid line coupler configured to attach to a first fluid line, a proximal end of the second lumen comprises a second fluid line coupler configured to attach to a second fluid line and a proximal end of the third lumen comprises a third fluid line coupler configured to attach to a third fluid line.

In another example, a respiratory insertion device includes an integrated tracheostomy tube. Here the insertion device may have an elongate body, the body having an elongate axis extending proximally to distally, an inflation cuff near a distal end of the elongate body, a central lumen within the elongate body, a first lumen extending proximally to distally along the elongated body having a first opening facing inwards towards the central lumen/passageway (between the first lumen and a central lumen that serves as a tracheal tube), a second lumen extending proximally to distally along the elongated body having a second opening into the second lumen on an outside of the elongated body distal to the inflation cuff, and a third lumen extending proximally to distally along the elongated body having a third opening into the third lumen on an outside of the elongated body proximal to the inflation cuff. Similar to previous examples, a proximal end of the first lumen may comprise a first fluid line coupler configured to attach to a first fluid line, a proximal end of the second lumen may comprise a second fluid line coupler configured to attach to a second fluid line and a proximal end of the third lumen may comprise a third fluid line coupler configured to attach to a third fluid line.

BRIEF DESCRIPTION OF THE DRAWINGS

FIG. 2 illustrates one example of a fluid management system, along with a respiratory insertion device, that automatically and periodically monitors and removes fluid from multiple regions along a tracheal tube.

FIG. 19B illustrates a spiral embodiment of a respiratory insertion device.

FIG. 19C illustrates a spiral-shaped respiratory insertion device for use with a tracheal tube.

FIG. 19D shows a close-up view of regions of the respiratory insertion device of FIG. 19A.

FIG. 22A illustrates a ring-type embodiment of a respiratory insertion device with suctioning lumen.

FIG. 22B is an alternative perspective view of the ring-type embodiment of the respiratory insertion device with suctioning lumen of FIG. 22A.

FIG. 22C is an enlarged drawing of a portion of the ring-type embodiment respiratory insertion device with suctioning lumen.

FIG. 24A is an offset view of yet another embodiment to the clip respiratory insertion device comprising two materials.

FIG. 24B is a side view of another embodiment to the clip respiratory insertion device comprising C-shaped supports.

FIG. 26A is a front and perspective view of an embodiment of a clip respiratory insertion device having stacked lumen.

FIG. 26B is a side view of the free clip respiratory insertion device of FIG. 26A having stacked lumen.

FIG. 26C is a side view of a clip respiratory insertion device having stacked lumen engaged with a tracheal tube.

FIG. 27A is a side view of an oropharyngeal airway insertion body.

FIG. 27D shows a section view through the proximal end of the insertion body of FIG. 27A.

FIG. 27B is another view of the oropharyngeal airway insertion body.

FIG. 27C is a third view of the oropharyngeal airway insertion body showing suctioning ports.

FIG. 28A is a side view of an integrated respiratory insertion device showing a first suctioning region.

FIG. 28B is a side view of the integrated respiratory insertion device of FIG. 28A showing a second suctioning region.

FIG. 28C is a side view of the integrated respiratory insertion device of FIG. 28A showing a third suctioning region.

FIG. 28D is a depiction of a section through the proximal end of the integrated respiratory insertion device of FIG. 28A.

FIG. 28E shows a distal end of the integrated respiratory insertion device of FIG. 28A.

DETAILED DESCRIPTION

Figure 1B:
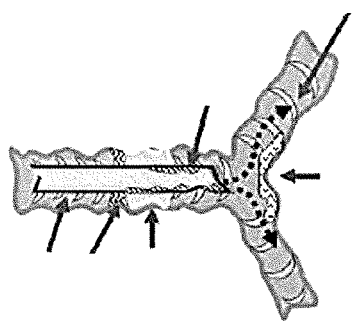
FIG. 1B illustrates a trachea and a bronchi region, showing different regions where fluid can collect.
Figure 1D:
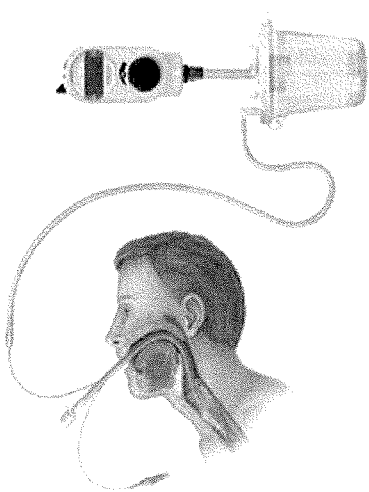
FIG. 1D illustrates a traditional tracheal tube system that requires manual suction and subglottic secretion drainage
Figure 1A:
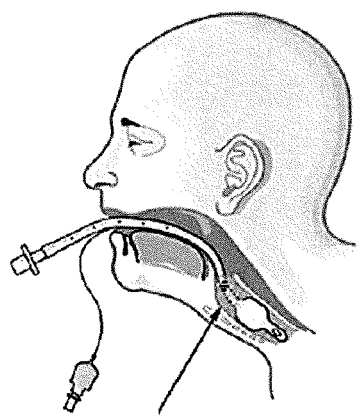
FIG. 1A illustrates a traditional endotracheal tube (tracheal tube) that has been inserted into a patient where the arrow shows a pocket of fluid build-up.
Figure 1C:
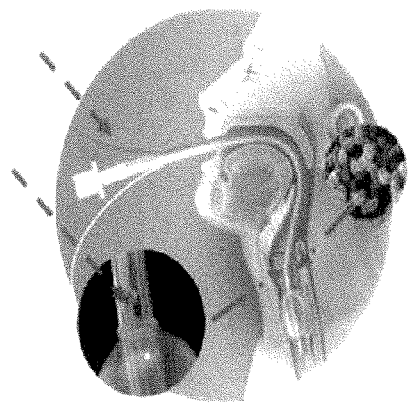
FIG. 1C illustrates a traditional fluid removal set-up that only suctions a subglottic region of the patient.

Described herein are systems and devices for managing unwanted fluid collection along a tracheal tube. In general, the fluid management system may include a controller, a plurality of fluid lines, a plurality of flow sensors, a plurality of pressure sensors, a lavage subsystem, and at least one secretion collection jar. In some embodiments, the fluid management system may also contain a display for showing pressure values or keeping a user informed of where within the cycle the system is during operation. The system may also be adapted to display an analysis of secretions. Respiratory insertion devices may couple to any of the fluid management systems described. The respiratory insertion devices that will be described below may generally function to remove fluid build-up along certain regions of a tracheal tube. The respiratory insertion devices may be used in conjunction with an existing tracheal tube or may perform the function of the tracheal tube including tracheostomy tube in addition to working to manage fluid collection along the respiratory tract. In general, the system may include a controller, power source, pumps, valves, suctioning devices, sensors, fluid lines, display, and switches.

The system described herein can automatically remove fluid from multiple regions along a respiratory tract. The term automatically may refer to any act or function that is capable of operating independently (e.g., without ongoing input from a user). In some variations, the term automatically may indicate that some action is performed without manual intervention. This does not mean that no manual intervention is ever required, because in the present case, human intervention may be used to trigger or set the process that in all other respects can be automatic. In particular, a user can set the system to run at defined intervals or when certain conditions are met.

Fluid may refer to a substance that is capable of flowing and continually deforms under applied shear stress. Fluids can include liquids, gases, plasma, and some solids. As applicable here, the term fluid may be used synonymous with liquid, a substance that has a definite volume but no fixed shape. Thus, fluids may refer to biological liquids secreted from a person's oral and respiratory system, mainly saliva, mucous, gastric contents and lavage fluid.

Next, the system may include fluid lines that connect the respiratory insertion device with the fluid management system. Fluid lines may be any hollow body that can convey fluids, liquids, or gases from one location to another (e.g., tubing, channels, etc.). Fluid lines can be formed from metals, glass, rubber, and other synthetic or naturally-occurring material. Fluid lines may be flexible and formed of fluid impermeable, hollow, cylindrical bodies that couple the respiration insertion body to the fluid management system.

The respiratory tract may refer to regions associated with respiration on a mammal, specifically, a human. In general, "respiratory tract" can refer to the upper respiratory tract and/or the lower respiratory tract. The upper respiratory tract can refer to parts of the respiratory system above the glottis (vocal cords) while the lower respiratory tract consists of the trachea, bronchi, bronchioles, and lungs. The respiratory tract may refer to the oral cavity, the glottis, the trachea, and the region directly above the bronchi.

As discussed above, a tracheal tube may refer to a hollow tube that can be inserted into a trachea of a patient, primarily to establish and maintain the patient's airway and to ensure adequate respiration. In general, tracheal tubes may include endotracheal tubes and tracheostomy tubes.

A controller may generally refer to a device that can interface with peripheral components and manage how the peripheral components interact and work in connection with each other. The controller may include circuitry (e.g., chip, chipsets, cards, and the like) for sending commands to the components present with the fluid management device. The controller may contain logic gates, routine/subroutines, and data storage components for running the monitoring and suctioning programs. The controller may also include external user interfaces such as displays, buttons, and switches.

Sensors generally refer to a component that can detect a certain characteristic of the environment it is in. In particular, described herein are flow and pressure sensors. Flow sensors may be configured to detect the presence or absence of fluid. Flow sensors can be differential pressure flowmeter, velocity flowmeters, positive displacement flowmeters, mass flowmeter, or open channel flowmeter, IR based sensors, capacitive sensors, and UV sensors. Pressure sensors may detect pressure and may include, but not limited to absolute pressure sensors, gauge pressure sensors, vacuum pressure sensors, differential pressure sensors, and sealed pressure sensors. Some pressure sensors are force type sensors that collect a force value to measure strain when pressure is applied to the area and include piezo resistive strain gauge, capacitive, electromagnetic, piezoelectric, optical, and potentiometric. Other non-force collecting pressure sensors may include resonant, thermal, and ionization-type pressure sensors. As with any type of sensor, calibration will help in accurately determining the value associated with the condition detected. Finally the flow and pressure sensors may be either internal or external to the fluid management system. One possible position is where the flow and pressure sensors are placed on fluid lines of the system in relative close proximity to where the system couples to the respiration insertion device. Other potential locations for the flow and pressure sensors may be within the controller unit body.

Lavage may refer to rinsing out a body cavity with water or a medicated solution either to clear away unwanted materials or for diagnostic purposes. As described herein, lavage may occur at various pre-determined regions along the respiration insertion device. For example, the apparatuses described herein may apply lavage to the oral cavity and the oropharynx region on a patient.

Fluid Management Systems

In general, a fluid management system may include fluid lines, sensors, a controller and circuitry for the controller, and lavage components. The controller is typically the portion of the fluid management system that oversees operation of the fluid management system components. The controller may contain circuitry and micro-controls for regulating fluid removal, in the case of suctioning fluids away from a region along the tracheal tube, or fluid delivery in the case of lavage of a certain region of the oral cavity or respiratory tract where the tracheal tube has been inserted. The controller may contain valves that connect and maintain fluid lines that link the respiratory insertion device to sensing, suctioning, and pumping components of the fluid management system. In use, the controller may also include micro-controls that contain circuitry for coordinating the sensing, suctioning, and pumping cycles. The controller periodically, automatically, and independently apply pressure, suctioning, or sensing to each fluid line The fluid management system also contains fluid lines that connect the respiratory insertion device with the sensing, pumping, and suctioning components of the fluid management system. The fluid lines can be arranged in multiple configurations. In some examples, separate fluid lines connect to each of the ports contained on the respiratory insertion device. In other examples, more than one port on the respiratory insertion device can be connected to one fluid line via a multi-port component. The fluid lines should be flexible such as surgical tubing, pressure tubing, or the like. While no preference for fluid line materials are noted here, it would be useful for the fluid lines to be able to withstand suctioning without the walls of the tubing collapsing or withstanding pressure without having the line break from the applied pressure.

The fluid management system typically also contains sensors that allow the system to determine the presence (e.g., by flow) of secretions in the fluid line (presumably removed from the pre-determined regions along the tracheal tube), and/or to regulate the amount of pressure or suction being applied. Flow and suctioning sensors may be present to sense the presence/absence of secretions flowing past the sensors. The sensors may be configured to provide analogue/digital signals to the controller The fluid management system may then compare the signals sensed with pre-programmed values entered by a user or manufacturer to keep the system running till it senses the presence of secretions.

The controller may incorporate a power supply that drives the fluid management system components. In the case where the power supply is integrated into the body of the controller, buttons and switches can be found on the body of the fluid management system that allows the user to control the fluid management system. In other examples, the power supply is externally maintained and is connected to the fluid management system when in use. The fluid management system may also contain internally or externally-maintained pumping and suctioning mechanisms.

Next, the fluid management system may include a lavage mechanism for rinsing out a void region associated with the tracheal tube. Lavage of an area that is in contact with a tracheal tube and where fluid or moisture may help decrease the amount of harmful microbes that might accumulate. While lavage of a patient's oral cavity is most common, lavage of other regions along a tracheal tube such as the oropharynx region or the subglottic region is also possible. The fluid management system includes fluid lines that connect to the respiratory insertion device to deliver and subsequently suction the lavage fluid from the void region. The fluid for lavage can be sterile water, saline, chlorhexidine or other suitable solution.

The fluid management system may also contain analysis components that can test the fluid withdrawn from the different regions along the tracheal tube of a patient. The fluid management system may contain pre-programmed subroutines that may periodically test the withdrawn fluid for certain types of harmful microbes. If detected, the fluid management system may include a way of notifying the doctor or caregiver of the potential for infection based on the positive test for the harmful microbe(s) or analyzing the viscosity, volume and/or color of the fluid extracted.

Fluid management systems may also include one or more secretion collection containers (e.g., jars, chambers, cups, etc.). Secretion collection jars may be placed in different locations with respect to the other components of the fluid management system as will be discussed in more detail below. Further, there may be a single secretion collection jar that collects all the fluid from the different regions along the respiratory insertion device or there may be separate individual fluid collection jars that correspond to fluid collection from the different regions. There may also be a separate fluid collection jar for receiving lavage fluid. The fluid obtained may be discarded or sampled to test for presence of microbes. In some examples, collection jars may also include a fluid level sensor for detecting when the liquid has reached a certain level and provide alerts to the user to empty the collection jar or jars.

In use, the system starts with sample suctioning at a predefined time period (which is adjustable and can be set by the physician based on the clinical judgement and condition of the patient). During the sample suctioning the control unit switches ON the suction valves and the suction begins for a minimum set amount of time (pre-set by the physician or manufacturer). During this sample suctioning stage, secretion fluids (saliva, mucous, gastric reflux or any other bodily fluid) are sucked out up till the sensing unit which is near to the head of the patient. The sensing unit senses the flow/presence of fluid and keeps the suction ON until it senses that the flow/presence of fluid/secretions has decreased to a pre-set value. This fluid gets collected in the collection Jar.

When there are no more fluids/secretions in the patient's oral cavity/oropharynx/subglottic (above the cuff) and/or inside the tracheal tube main lumen, the sensor unit may sense the absence of secretions in the tubing and checks for port blockage by the use of pressure sensor. On detection of port blockage a lavage liquid from the liquid container is injected in the blocked line by use of the pump and opening the valves. This fluid injected in the opposite direction to the direction of suctioning, unblocks the port. The injected fluid is immediately sucked out by use of the suction from the other two lines or by the same line.

In the case where none of the ports are blocked, the pressure sensor does not sense port blockage and the system concludes that there are no more secretions. It then turns off until the next cycle of sample suctioning.

The sheath/sleeve will have additional ports, or by using the ports in the oral cavity, lavage liquid is passed through the oral cavity at regular intervals pre-set by the physician (or in some embodiments, the manufacturer) to perform oral rinsing to maintain oral hygiene. The lavage liquid is suctioned out immediately by the same port/other ports. The device effectively reduces nurses/care givers contact with the patients trachea and thus reduces the chances of cross infection The device has built in software to calculate and analyze the volume, flow rate and viscosity of secretions and plot a graph of the patient's secretion pattern and detect and predict the onset of infection or detect early signs of infection. It is also possible to detect pathogens where the device has an additional feature of detecting the particular strain of bacteria/pathogen causing the infection by using micro fluidics based technology.

Figure 3:
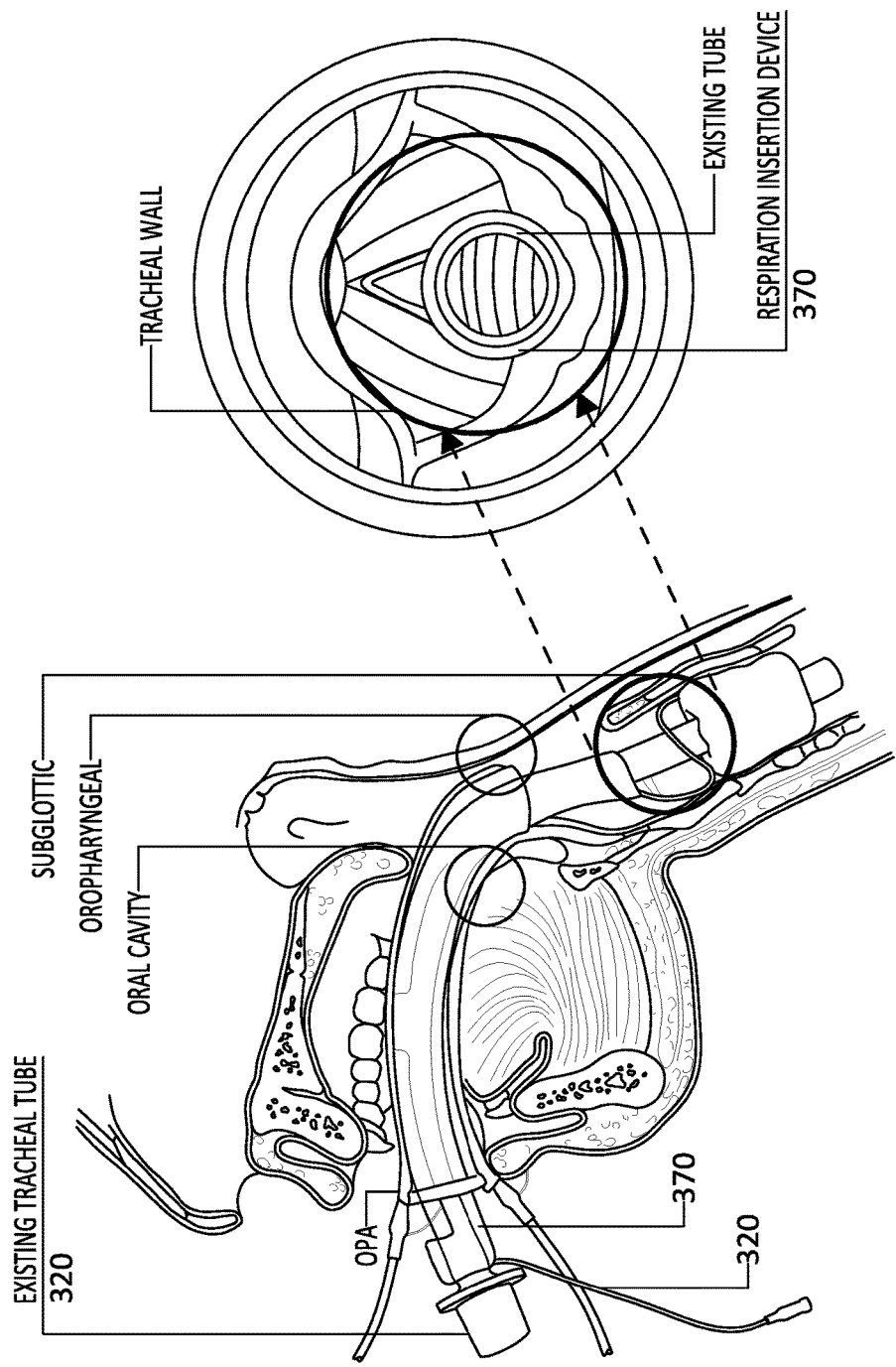
FIG. 3 illustrates an example of a respiratory insertion device of an automatic fluid removal system inserted through a subject's mouth (shown in cross-section) and the opening created within a patient's trachea.
Figure 4:
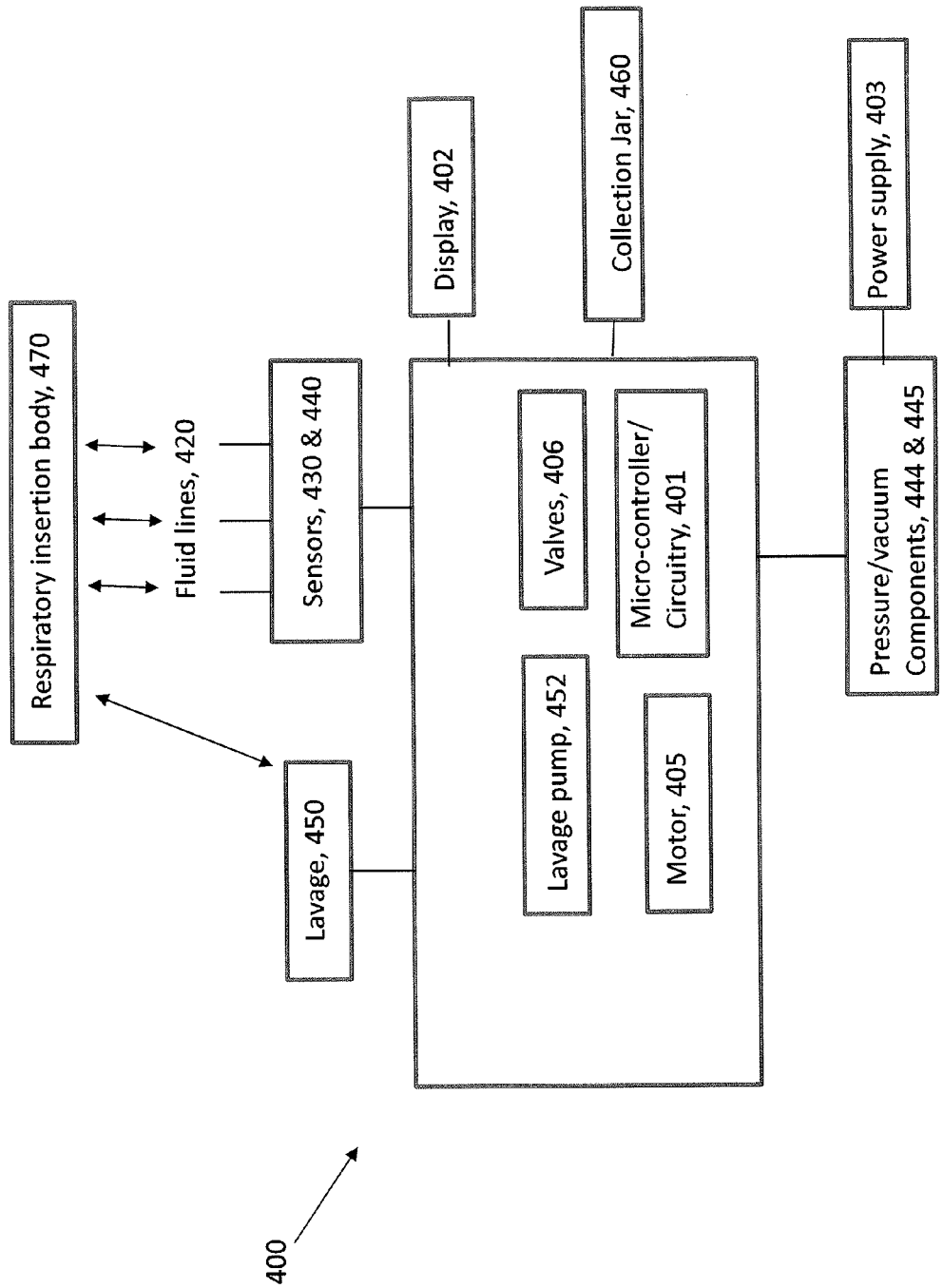
FIG. 4 illustrates a generic fluid management system as described herein.

The device can share data through USB, internet, WiFi, Bluetooth, Ethernet, memory stick, or any other data transfer technologies and has a small printer attachment to print out hard copies of the infection graph of the patient Turning to FIGS. 2 and 4, a general embodiment of the fluid management system 200 and a respiratory insertion device 270 is shown. In this particular example, there are three fluid lines 220 that couple to respiratory insertion device 270. Further discussion of the various embodiments of the respiratory insertion device and how it connects to the fluid management system as well to existing tracheal tubes will be discussed in greater detail below. The fluid management system shown in this example has an integrated controller 201 that includes flow sensors 230 and pressure sensors 240 (not shown). Also included but not shown here are pressure controls 242 and suctioning/vacuuming controls 232 for detecting and removing fluid pooling in the pre-set regions along the tracheal tube. Also shown is a single secretion collection jar 260. As previously mentioned, while the fluid management system is capable of separately collecting fluid withdrawn from the pre-set regions along the tracheal tube, a user may easily combine the fluid through separate fluid lines 220 into one fluid collection jar 260. FIG. 3 provides a better view a respiratory insertion device 370 in an intubated patient with an existing tracheal tube. The pictorial shows a cross-section of a patient's oral, oropharyngeal, and subglottic regions having and regions along the tracheal tube and the patient's respiratory tract that corresponds to fluid accumulation and where respiration insertion body can monitor and remove fluid.

FIG. 4 shows a general schematic of a fluid management system 400 and its major components. The location and connections between the components shown are illustrative and meant to point out to the reader general locations of these components. The components may be arranged and coupled in a variety of ways that are suitable for managing fluid accumulation in an intubated patient and will be discussed in greater detail below.

Finally, any of the fluid management system may incorporate lavage as a complement to removing fluid secretions around the tracheal tube. Lavage can be applied to the oral cavity, the oropharynx, or subglottic region of the patient to moisten areas where saliva would normally bathe but cannot in the case of an unconscious, intubated patient. Lavage can be used to periodically wash the above mentioned regions to clear out debris and microbes that may cause infection. The fluid and suctioning lines for lavage can be in addition to what is already present for sensing and removing fluid from the oral, oropharynx, and subglottic regions and have separate pumping and suctioning components within or external to the controller. In some instances, the lavage lines can tap into and share existing fluid lines.

Figure 5:
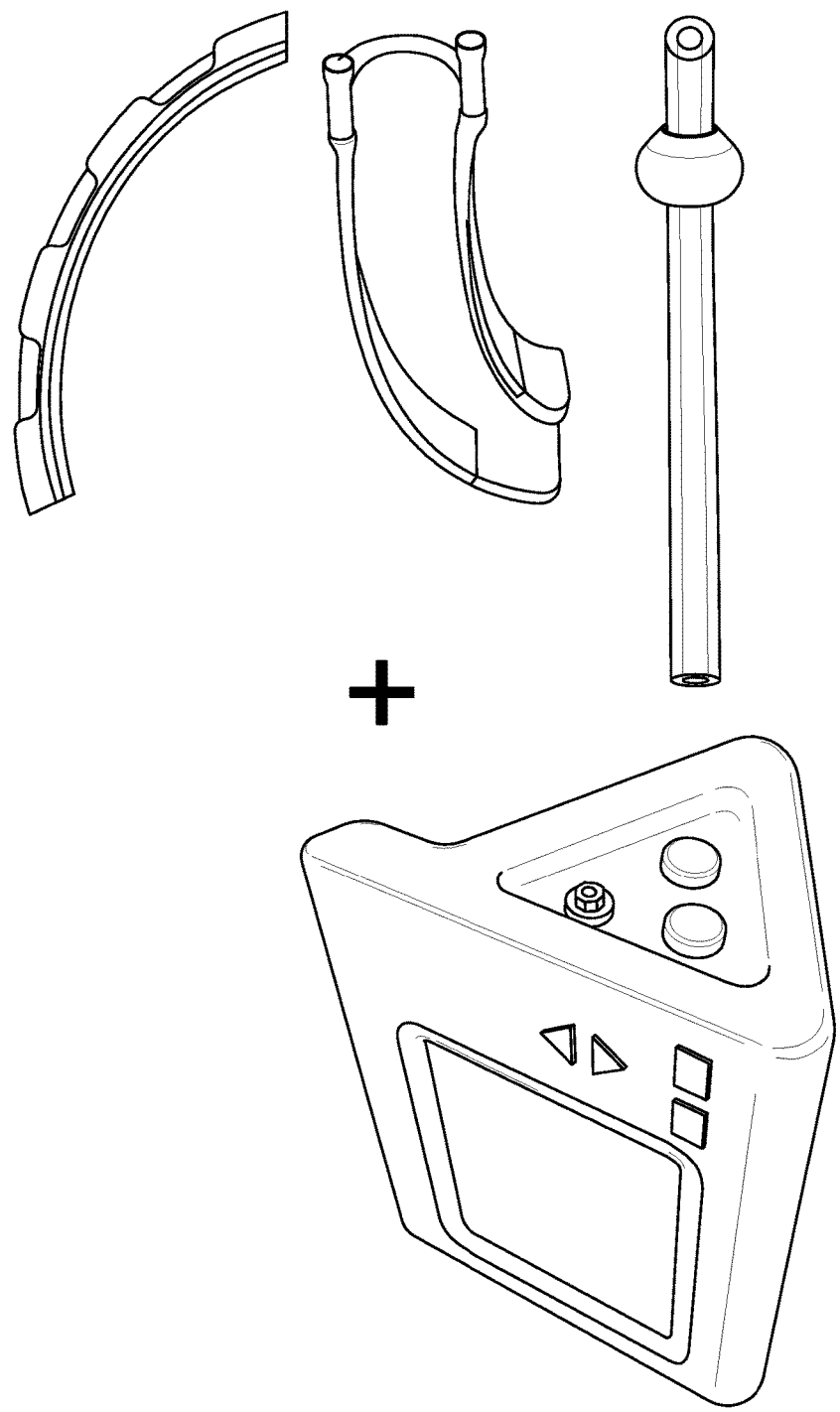
FIG. 5 illustrates one embodiment of a fluid management system that can be used in combination with various embodiments of a respiratory insertion device (three are shown on the right).
Figure 6:
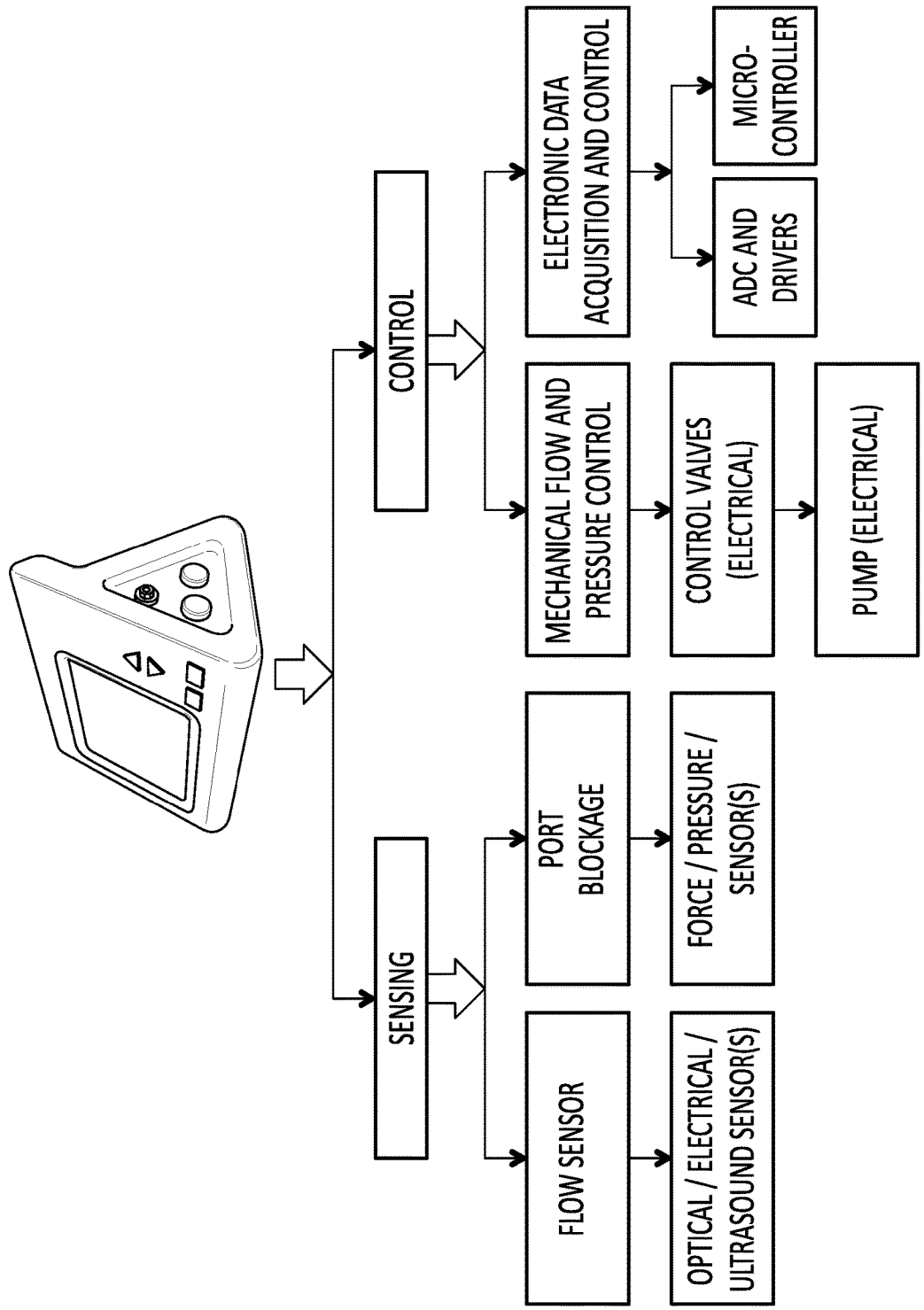
FIG. 6 illustrates two aspects of a fluid management system, including sensing and control components.

FIGS. 5 and 6 show the fluid management system unit as it has been currently conceived and reduced to practice. In FIG. 5, a representative number of respiratory insertion devices are shown to indicate that the fluid management system can be used with any of the respiratory insertion devices that will be described below. The overall goal of the fluid management system is to sense and control the amount of fluid secretions from an intubated patient that collects along the tracheal tube.

The sensing aspect of the fluid management system may contain two types of sensors. The flow sensors may be used to determine the flow at a particular instant in the tube, whereas the pressure sensors may be used to determine port blockage after the flow sensors have detected absence of secretions. Simultaneously, the pressure sensors can register pressure values associated with any of the fluid lines connecting to the respiratory insertion device and report the value(s) back to the controller. A routine within the controller can be initiated to compare the detected pressure with preset values such that if the detected pressure is lesser than the pre-set value, blockage or fluid collection is indicated at a particular region along the respiratory insertion device. Sensors can be placed in any appropriate region, including at the port openings of the respiratory insertion device or along the fluid lines to sense whether there is fluid present at these locations. As mentioned, sensors may be non-contact, e.g., configured outside of the fluid line, so that they do not contact fluid within the fluid line(s). If fluid flow (and therefore fluid) is detected and reported back to the controller, the controller can initiate a set of instructions for clearing the fluid. In this configuration, the pressure sensor may detect blockage only in the case when the flow sensors first detect that there is no secretions.

The control aspect of the fluid management system regulates the mechanical and pressure flow within the system. As FIG. 6 shows, solenoid valves in connection with at least one pump are used to control the flow of fluid within the fluid management system and the respiratory insertion device. Also maintained within the fluid management system module are electronics for collecting and retaining information associated with frequency of monitoring for blockage. There may also be internal tests that detect presence of potentially harmful microbes within any of the fluid lines. Information on the status of the fluid management system can be displayed on an integrated monitor or can be shown on a separate monitor.

Figure 7:
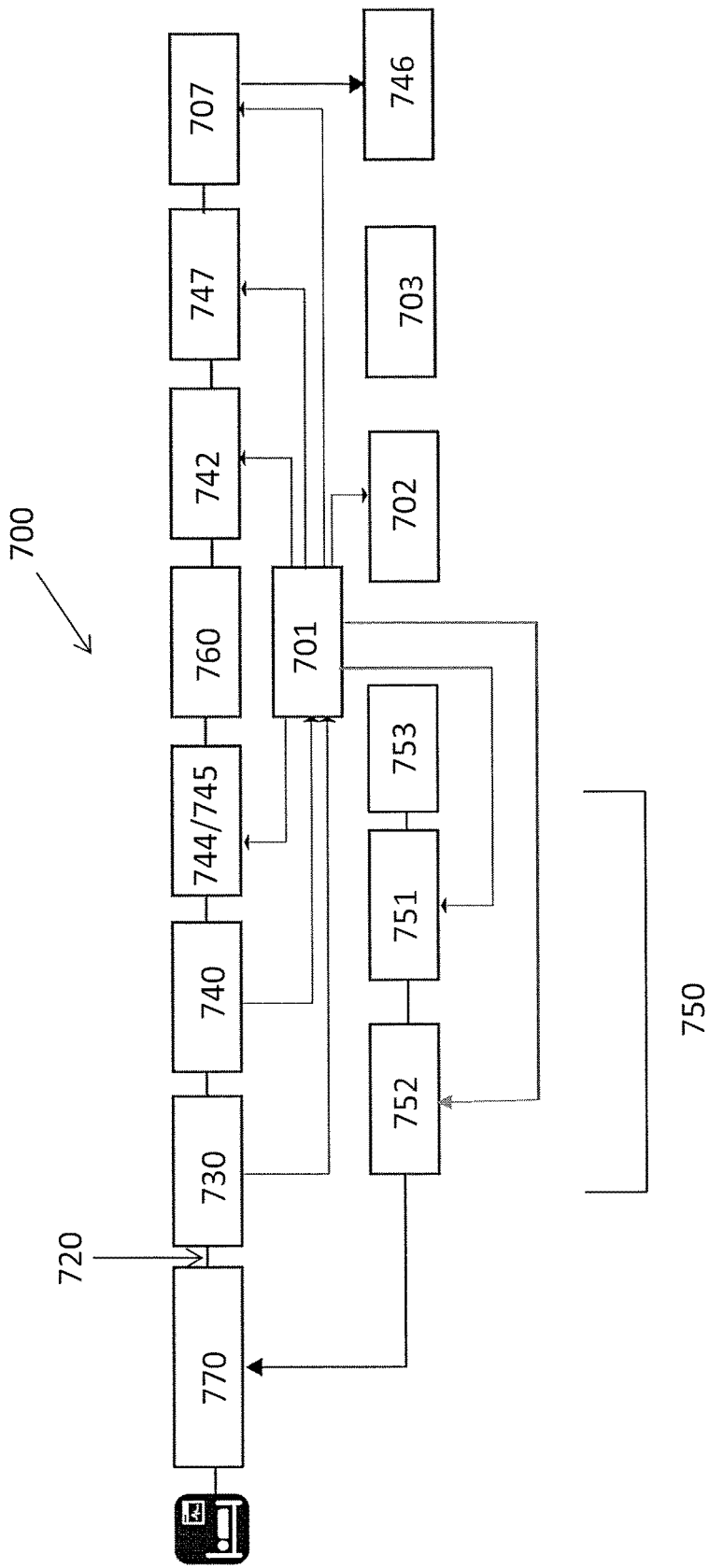
FIG. 7 is a block diagram of one embodiment of the fluid management system showing a controller in connection various components (including the tracheal tube 770, a flow sensor 730, a pressure sensor 740, a pressure control mechanism 742, control valve(s) 744/745, vacuum 707, lavage 750, a display 702 and a power source 703).

A first embodiment of the fluid management system is shown in FIG. 7. A controller 701 links all of the other components present. A respiratory insertion device 770 can be an integrated tracheal tube, a sheath, or one of the other arrangements that will be discussed below. The respiratory insertion device may be arranged as the primary tracheal tube or an attachment to an existing tracheal tube within a patient. Respiratory insertion device 770 may include at least two lumen for suctioning two different regions along a tracheal tube. Respiratory insertion device 770 is fluidly connected to the remaining fluid management system 700 components via fluid lines 720. Adjacent to respiratory insertion device 770 are flow sensors 730. Flow sensors detect the flow/presence of secretions at an instant at the particular location and aid in switching off the device, if they sense absence of secretions. The cycle starts at a predetermined time interval and keeps running till there is no more flow. Flow sensors 730 are associated with each line present within respiratory insertion device 770. Flow sensors 730 can detect whether there is still fluid present within the corresponding line within respiratory insertion device 770. Flow sensors 730 can automatically and continuously (within the given cycle) detect flow within their corresponding lines as part of a step-wise routine. Alternatively, a user can manually determine flow in any or all of the lines through selecting certain options provided within controller 701. In this present embodiment, the flow sensors 730 are shown to be in line with other components of fluid management system 700, but in other examples, the flow sensors may be associated with separate lumen within the respiratory insertion device. The flow sensors can be any suitable sensor that can detect and report back on flow and/or presence of secretions within a line. Examples of such sensors may include IR sensors, UV sensors, resistive sensors, capacitive sensors, ultrasound sensors, and Hall Effect sensors.

Staying with the embodiment shown in FIG. 7, fluid management system 700 also includes pressure sensors 740 and pressure controls 742. Pressure sensors 740 are able to detect the pressure within a corresponding fluid line that connects to a particular lumen of the respiratory insertion device 770. Controller 701 may include routines that test the pressure within the fluid lines automatically and periodically or manually at the request of the user. Pressure controls 742 may either create negative pressure within a line to assess the amount of blockage within a particular line or create positive pressure to aid in unblocking a particular line (from a pressure source 746). There may also be a pressure relief/release 747 within fluid management system in situations where the sensed pressure within a line is above a set threshold value. Having pressure relief/release 747 may prevent excessive pressure being exerted on the patient's respiratory tract or within the fluid connections of either the respiratory insertion device or the fluid management system.

The embodiment shown in FIG. 7 also includes a collection jar 760. While the box diagram does not indicate the possible number of collection jars, there can be one central collection where all of the extracted fluid can be retained or more than one collection jar. In the case where there is only one collection jar, corresponding multi-port valves will be used to connect the fluid lines to the collection jar. A multiple collection jar set-up may be more useful for revealing where the source of an infection and provide caregivers with a clearer idea of what region along the patient's respiratory tract to target treatment in case of infection. It may also be useful to include a volume sensor within all of the collection jars present such that when fluid with the jars reaches a certain level, a fluid level sensor can signal the controller to sound an alarm to notify the user that one or all of the collection jars require emptying.

Figure 8:
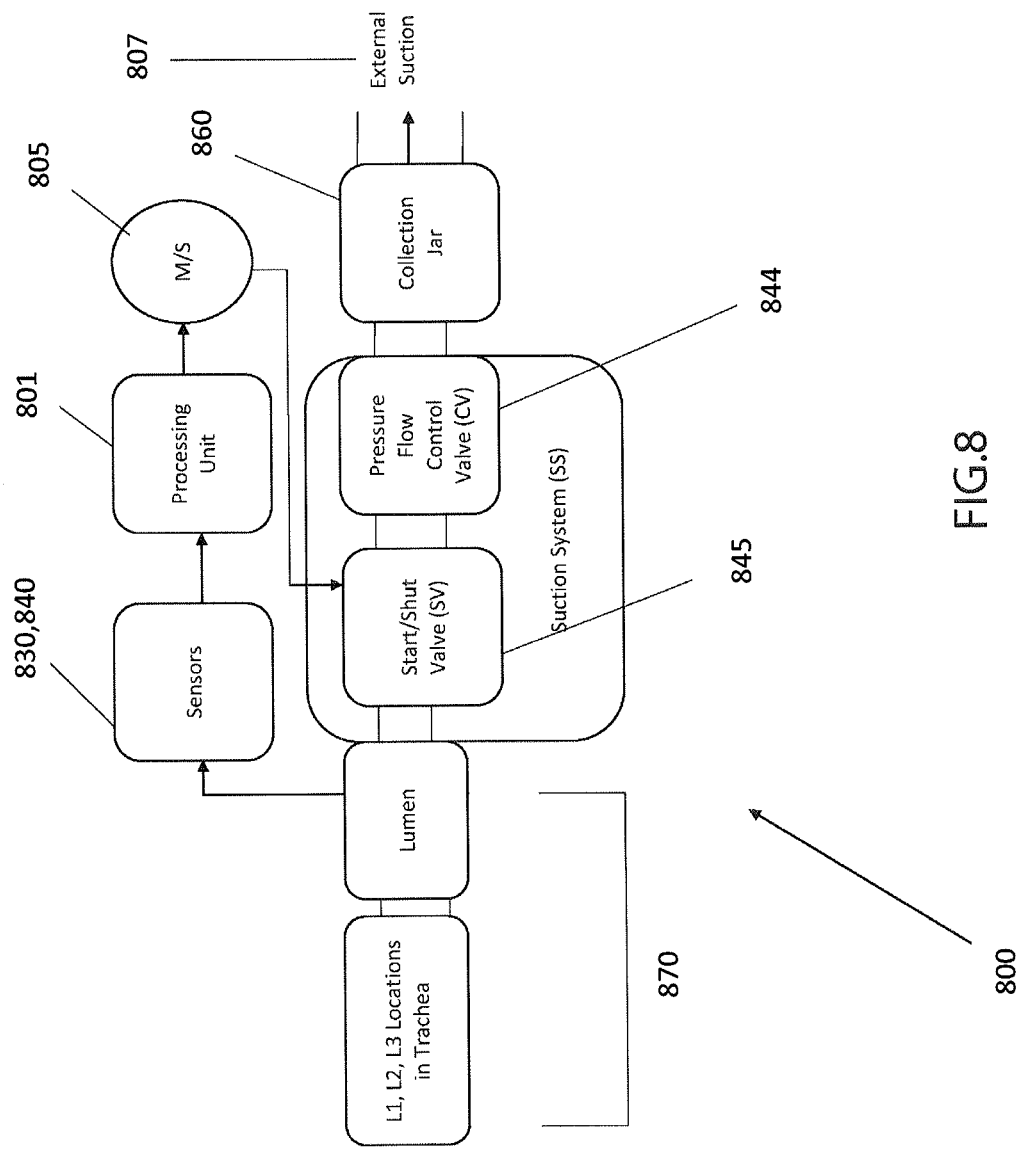
FIG. 8 is a block diagram of an alternative embodiment of the tracheal tube fluid management system for three regions of the trachea having an external suction.
Figure 9:
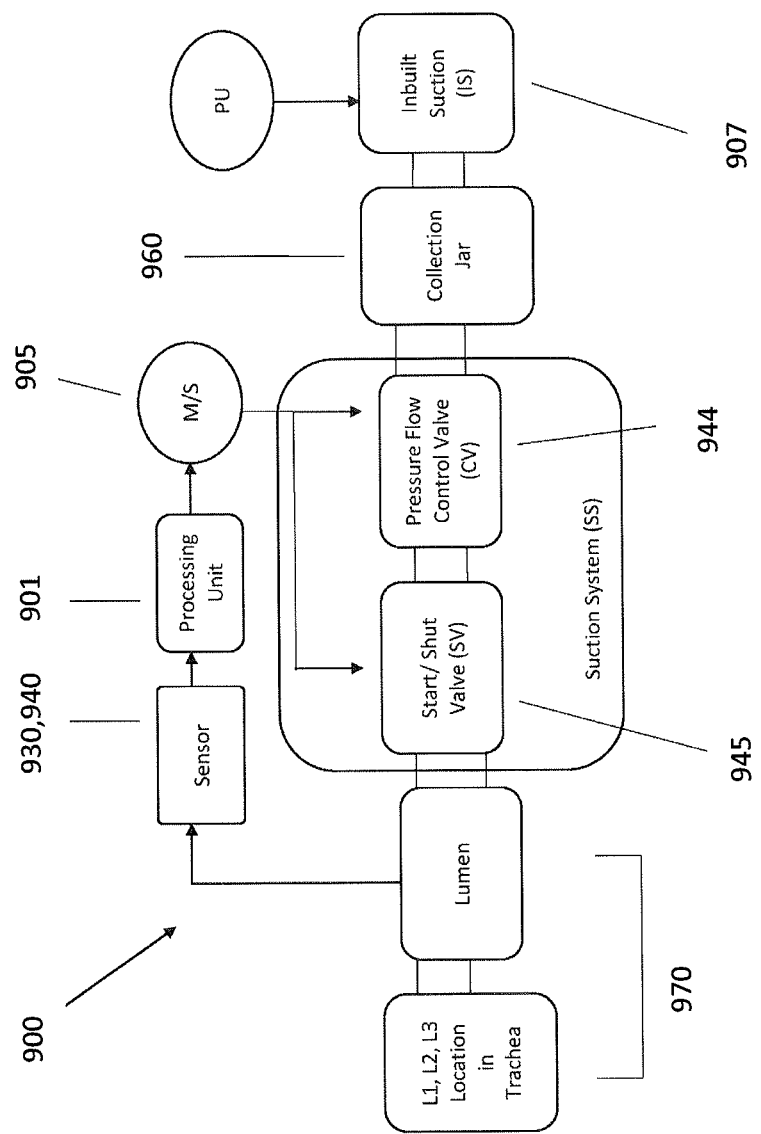
FIG. 9 is a block diagram of an alternative embodiment of the tracheal tube fluid management system for three regions of the trachea having a built-in suction.

A lavage system 750 is also present in the embodiment shown in FIG. 7. Lavage system 750 includes a lavage pump 751 and a lavage pressure control valve 752. Although not specifically shown here, lavage system 750 may deliver a rinsing fluid 753 to at least one region along respiratory insertion device 770. Controller 701 regulates lavage pump 751 and lavage pressure control valve 752 to deliver the rinse fluid at a desirable flow rate and pressure to the region or regions of interest. When the rinse portion of the lavage cycle is complete, lavage pump 751 can exert negative pressure to suction away the rinse fluid. While not specifically shown, an additional fluid line in connection with a collection jar can receive the post-rinse fluid. Alternatively, the additional fluid line can connect to any of the fluid collection jars already present within the fluid management system. FIGS. 8 and 9 show two possible arrangements of the suctioning features in the fluid management system embodiment discussed earlier. In FIG. 8, a suctioning feature is not included in fluid management system 800. In this arrangement, the suctioning or vacuuming feature is provided for externally. FIG. 9 shows the case where the suctioning/vacuuming is included within the fluid management system. While there are both advantages and disadvantages to both arrangements, neither greatly affect the overall functionality of the fluid management system. Finally, in both of the variations shown, the collection jars are situated after the suctioning and pressure valves. The advantage of having the suctioning and pressure valves in closer proximity to the respiratory insertion device is more precise control of the suctioning and pressure within the respiratory insertion device. The disadvantage of having the pressure and suctioning valves situated between the respiratory insertion device and the collection jar is that during suctioning, these valves may become more easily contaminated by the fluid passing through. Having the collection jar between the respiratory insertion device and the pressure and suctioning valves would minimize contaminating the valves but also provide less precise control of the pressure and suctioning that occurs at the distal end of the respiratory insertion device.

Figure 10:
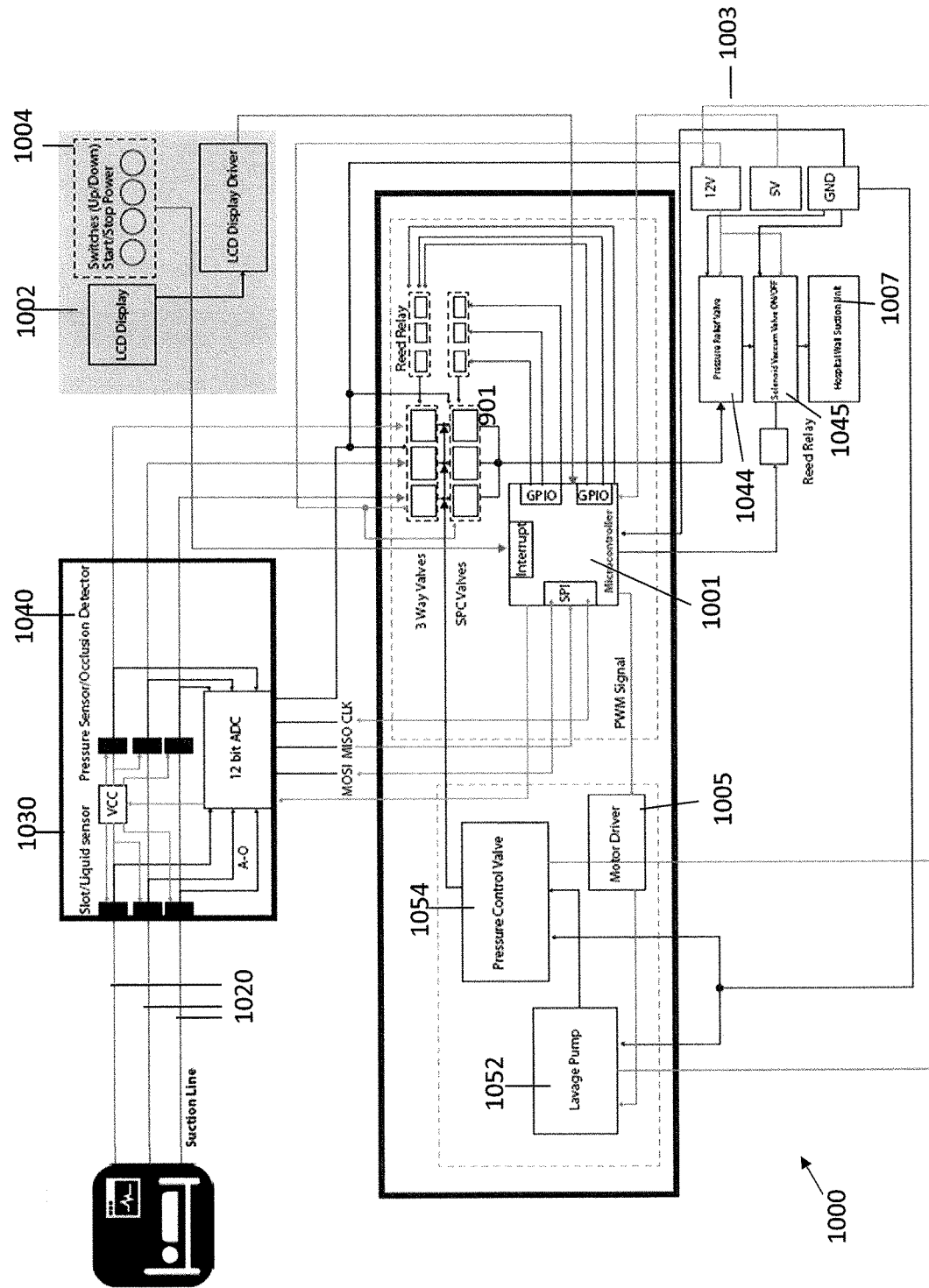
FIG. 10 is a circuit diagram of one variation of a fluid management system.
Figure 11:
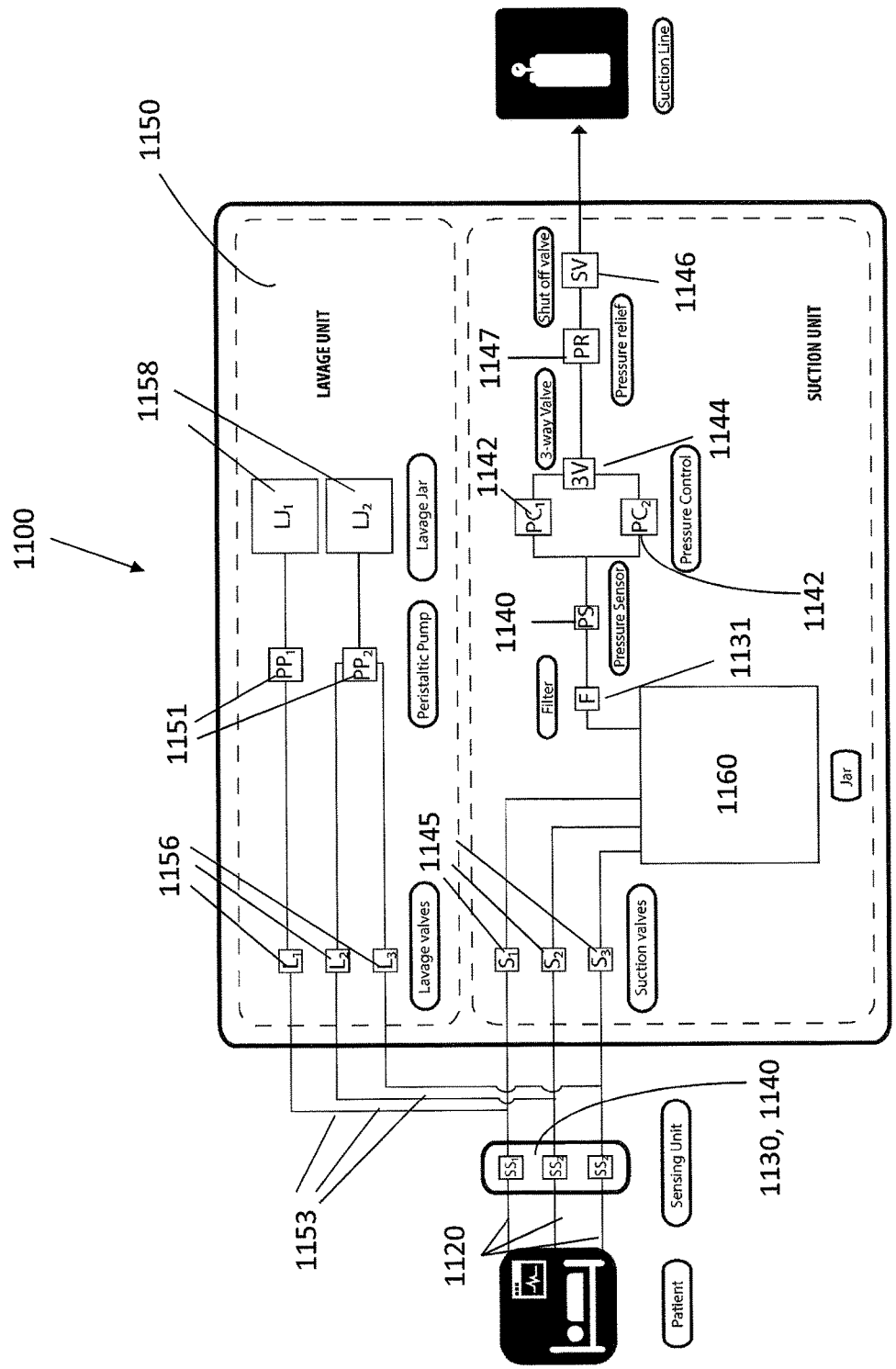
FIG. 11 is a block diagram of an embodiment of a fluid management system having the secretion collection vessels sensing units and a pressure sensor, and having six independent lines including three lines for suctioning and three lavage lines.

FIG. 10 shows a more detailed diagram of an embodiment of the fluid management system. While the system in FIG. 10 is similar to what is shown in FIGS. 7-9, the diagram in FIG. 10 indicates more than a general concept of the fluid management system and discloses in great detail the components used to reduce the fluid management system to practice.

FIGS. 11-15 show further variation in the arrangement of the collection jars and the various valves present within the fluid management system. In fluid management system 1100 shown in FIG. 11, the collection jars are placed before the suctioning and pressure valves. In system 1100, three separate lines emanate from respiratory insertion device 1170. Collection jar 1160 are associated with each line 1120. Collection jar 1160 can be a single jar or multiple jars, for example, a collection jar corresponding to each line. As previously mentioned, one of the main advantages of having the collection jars in front of at least some of the valves is that less contaminants reach those valves during suctioning, and requiring less frequent cleaning or replacement of these valves. There are also sensing units 1130, 1140 which sense pressure and flow and are associated with each fluid line. In many of the embodiments, filters are placed before the various modules to minimize contamination of these modules. System 1100 also includes lavage 1150 having three separate lavage lines 1153 that connect to the respiratory insertion device (not shown). The three lavage lines 1153 are controlled by a central lavage control valve 1152 and a lavage pump 1151. Also included is a lavage jars 1158 that contain lavage liquid where the lavage liquid can be pumped through to each of the lavage lines 1153 for rinsing out the different regions along the respiratory insertion device. It should be mentioned that the lavage control valve may only allow lavage liquid to pass to one or two of the lavage lines 1153 for rinsing. Control of which lavage lines receive rinsing fluid may be controlled by the operator or may be based on a detected value or condition set by the controller that then automatically signals the lavage system to activate. While not shown, lavage system 1150 may include a separate line for removing lavage liquid once lavage is completed or may utilize fluid lines 1120 for collecting used lavage liquid, here the lavage liquid is returned to collection jar 1160.

Figure 12:
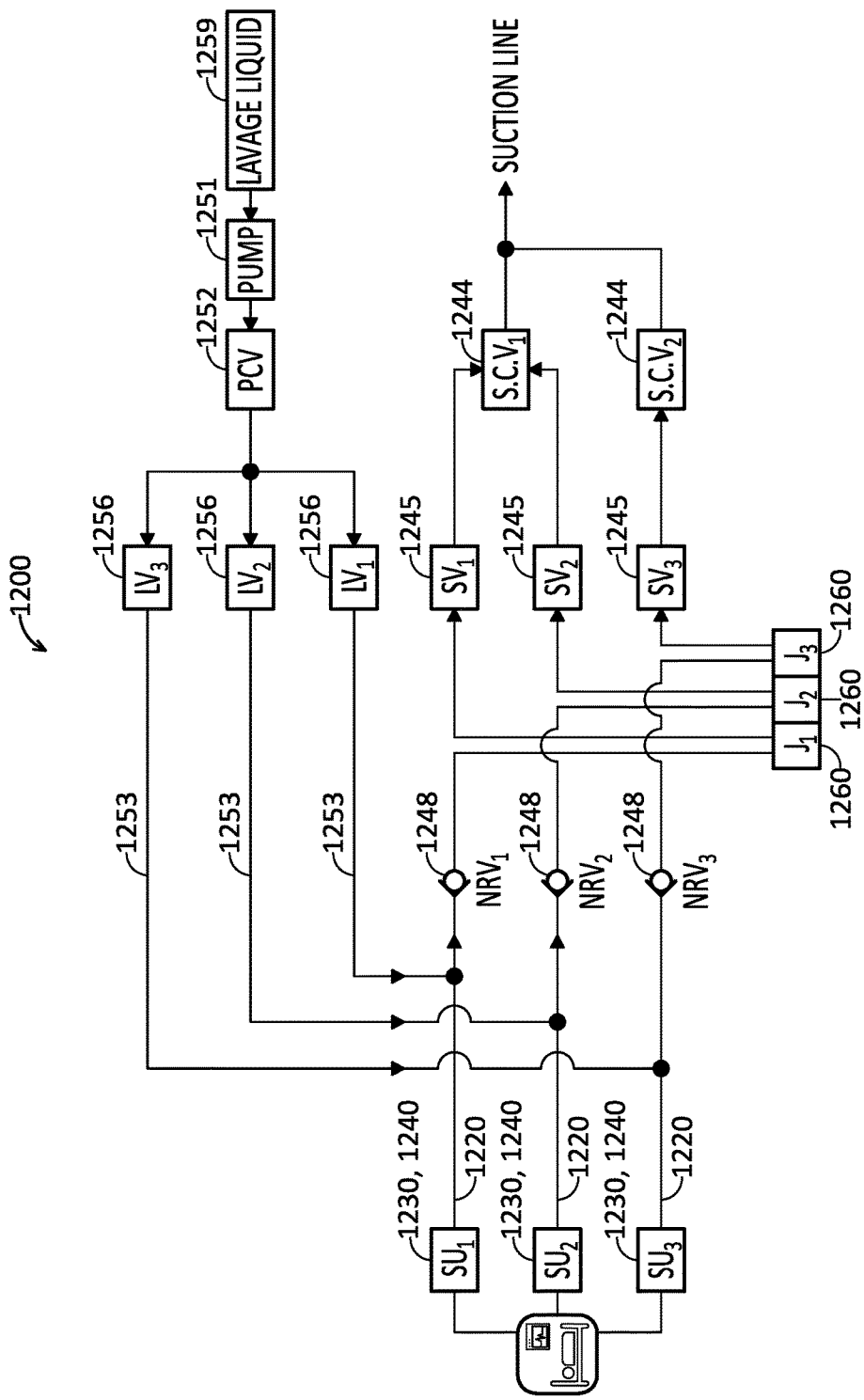
FIG. 12 is a block diagram of another variation of a fluid management system having non-return valves along each independent suctioning line.

FIG. 12 shows an alternative embodiment of the fluid management system setup. Similar to system 1100 setup, system 1200 has collection jars 1260 are situated before suctioning valves 1245. One notable difference in system 1200 is the lavage lines 1253 feed into fluid lines 1220 and not directly into the respiratory insertion device. As shown each lavage line 1253 taps into a corresponding fluid line 1220. In order to prevent lavage fluid 1259 from traveling toward suctioning valves 1245 instead of towards the respiratory insertion device during lavage, system 1200 includes a series of non-return valves 1248. When on, non-return valves 1248 forces lavage fluid toward the respiratory insertion device. For example, a non-return valve may have an on/off feature and may be operated to close the suction line only after there is pressure due to the lavage liquid; at other times the suction lines remain open.

Figure 13:
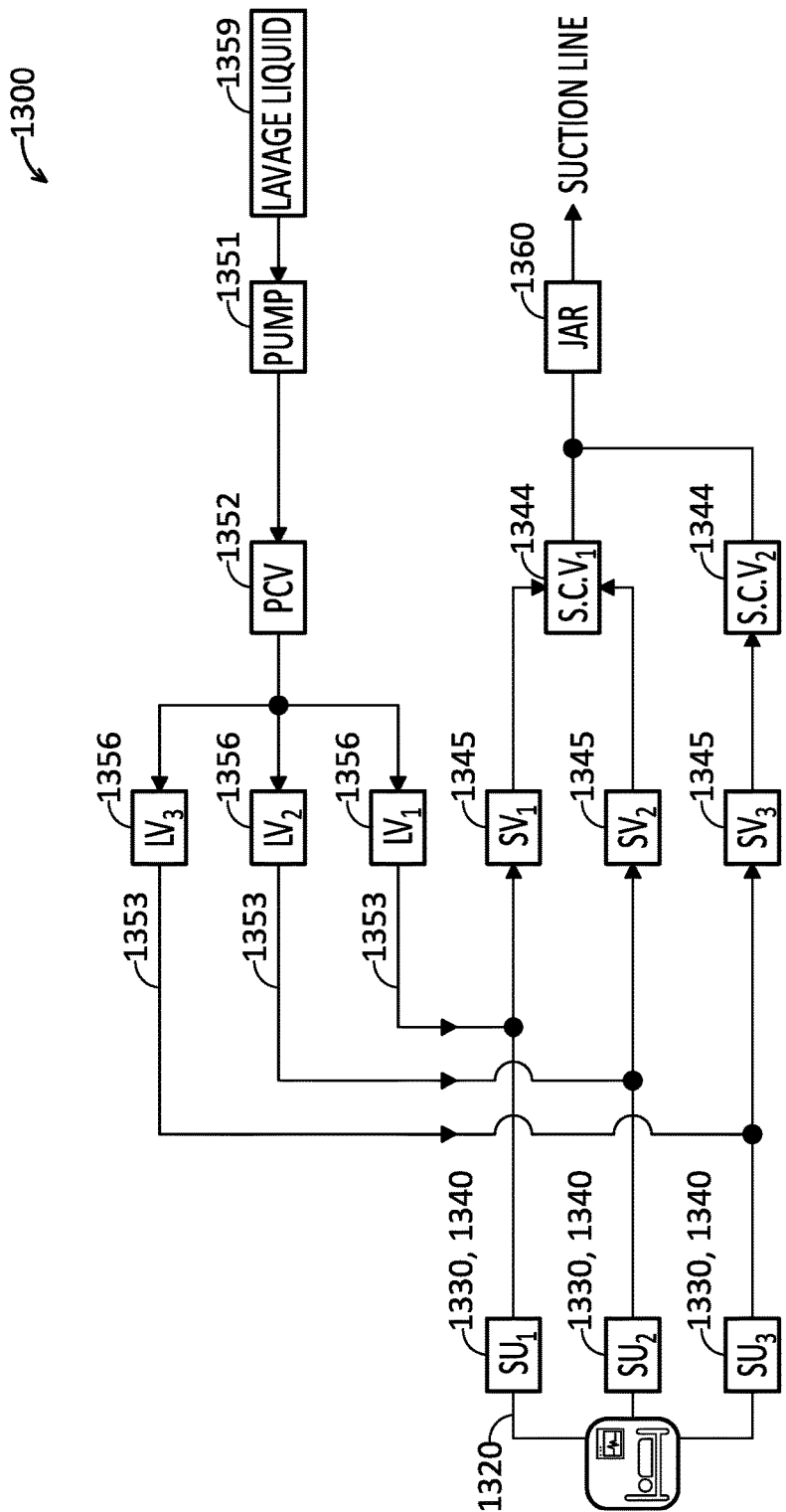
FIG. 13 illustrates an alternate embodiment of a fluid management system having the secretion collection jars behind the suctioning values and controls.

FIG. 13 shows yet another embodiment of the fluid management system setup. Similar to system 1200, system 1300's lavage 1350 is routed to corresponding fluid lines 1320 prior to reaching the trachea tube on the patient. In system 1300, a collection jar 1360 is placed behind suctioning valves 1345 and pressure valves 1344 are situated between collection jar 1360 and the respiratory insertion device. As previously mentioned, one disadvantage of having fluid lines 1320 contact suctioning valves 1345 and pressure valves 1344 is the greater chance for contamination. In order to minimize this effect, valves will be constructed having non-clogging components that will allow fluids of different density and viscosity to pass. In some examples, the interior of the valves can be coated with non-adhering material making it more difficult for microbes to attach. The valves can also be non-contact valves (e.g., pinch valves) and thus solve the problem of contamination as the valve body will never come in contact with the fluids and the valves will only pinch the fluid lines 720 to shut them.

Figure 14:
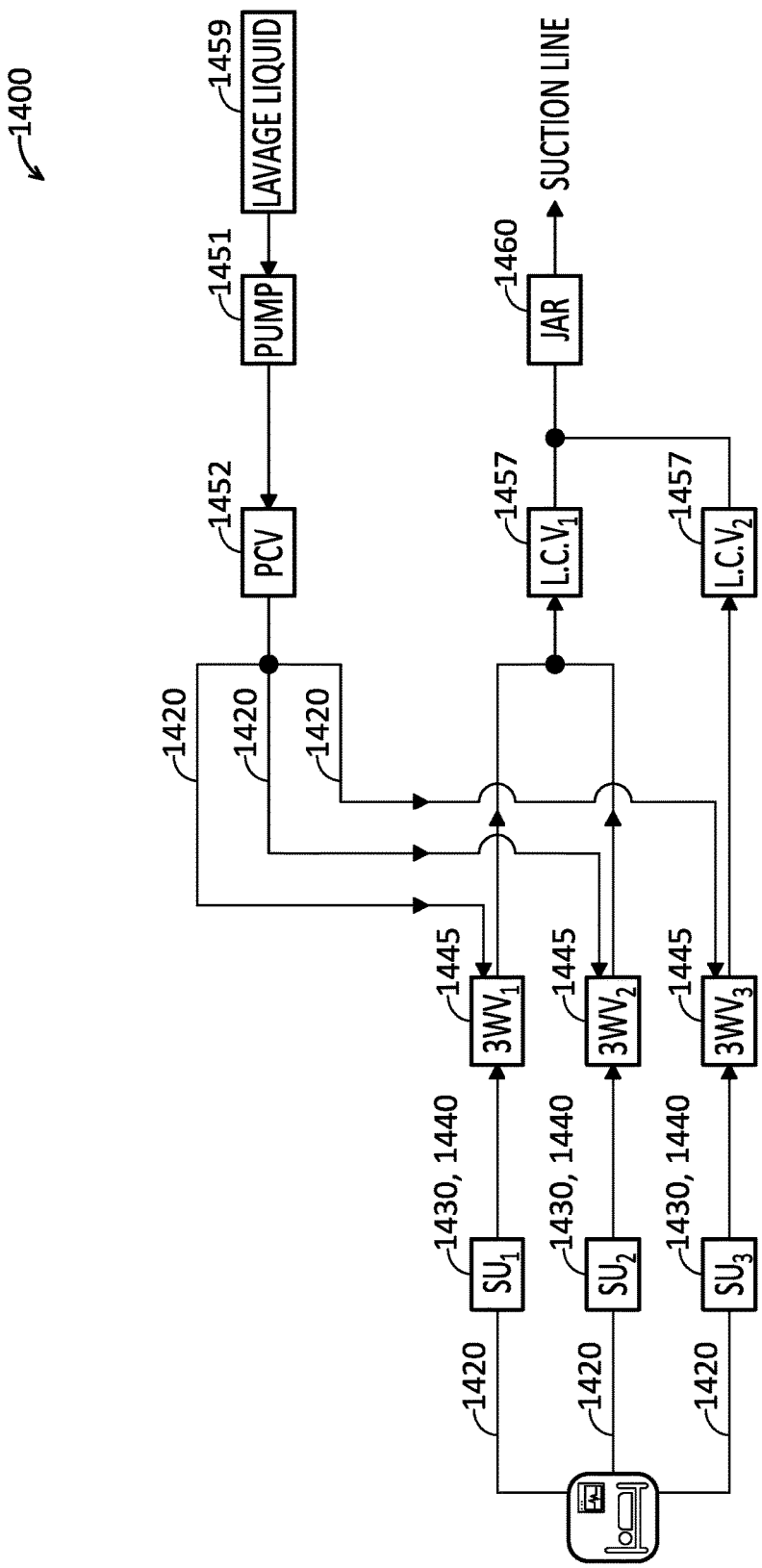
FIG. 14 illustrates an alternative embodiment of a fluid management system having one collection jar behind the suctioning lines, valves and lavage valves, using 3-way valves.

FIG. 14 shows a final fluid management system configuration having three fluid lines. In System 1400, jar 1460 is situated near the suction source and far away from suctioning valves 1445 and the respiratory insertion device. Suction valves 1445 are three way valves which allow different functions of the fluid management system to share some of the same lines which may decrease the space required within the fluid management system. System 1400 includes lavage lines (not shown in FIG. 14) that connect to rest of the fluid management components fluid lines 1420 between suction valves 1445 and jar 1460. System 1400 also include sensor units 1430 and 1440 for monitoring pressure and flow. System 1400 also includes additional suction control valves 1457 that may control the removal and flow rate of the used lavage liquid 1459 from the respiratory insertion device of the patient.

Figure 15:
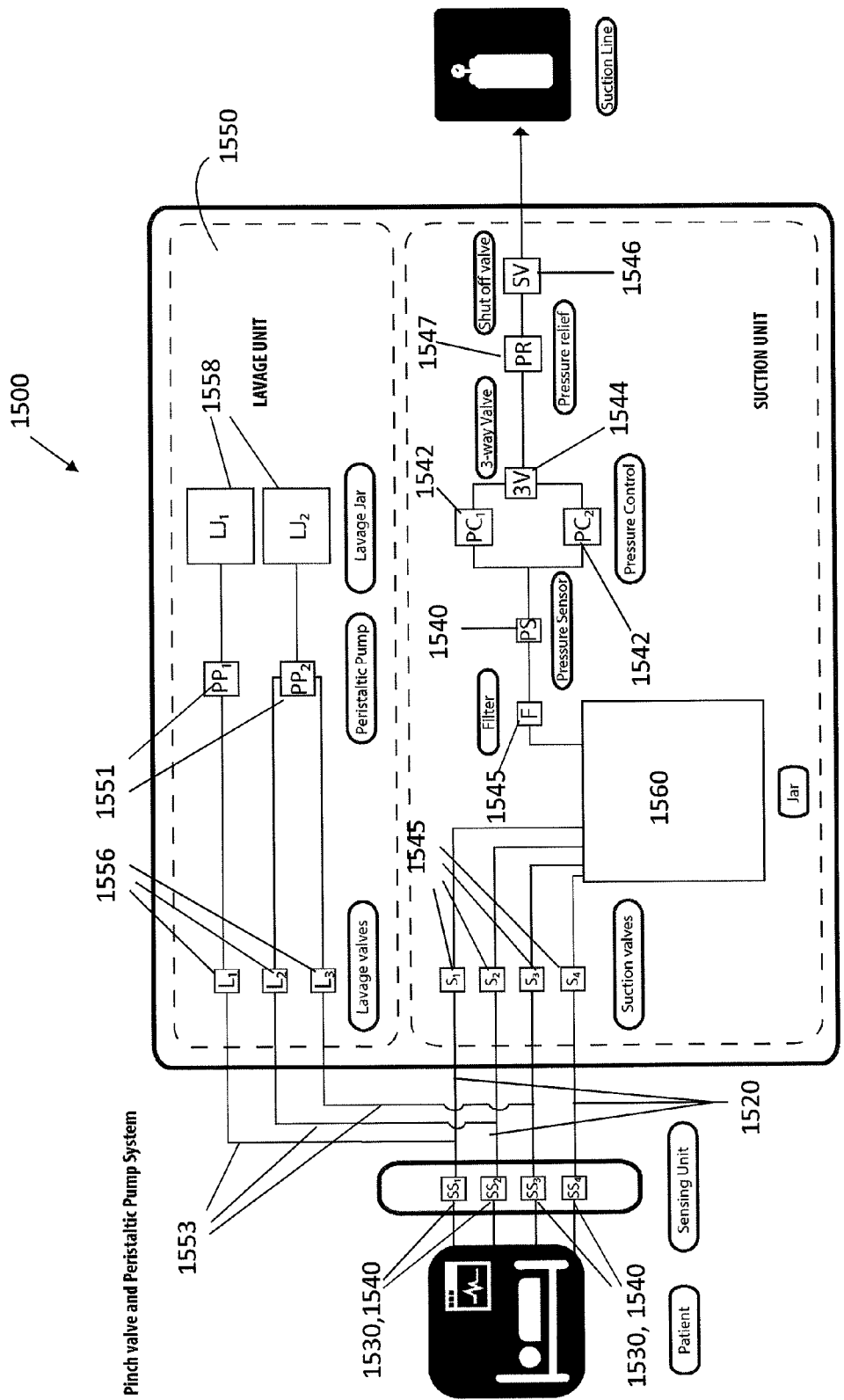
FIG. 15 illustrates an alternative embodiment of a fluid management system having four independent lines with corresponding sensors.

FIG. 15 shows a fluid management system embodiment having four independent fluid lines. The remainder of the fluid management system remain the same. In this embodiment, the extra fluid line can be used to remove fluid from a fourth location along the tracheal tube. Also, the additional fluid line may be used to remove fluid from within the actual tracheal tube as well.

Figure 16B:
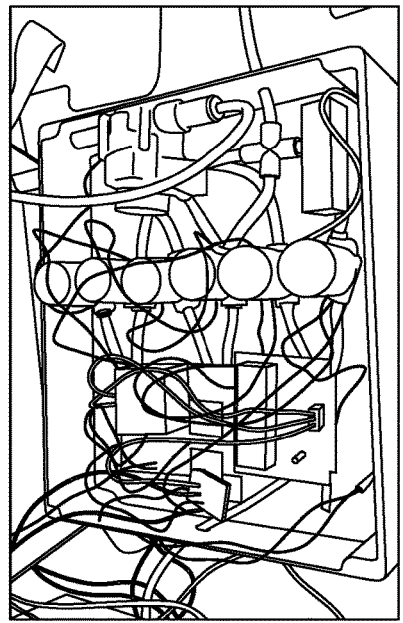
FIG. 16B is a close-up pictorial of the controller showing microcontroller, valves, pumps and circuitry.
Figure 16A:
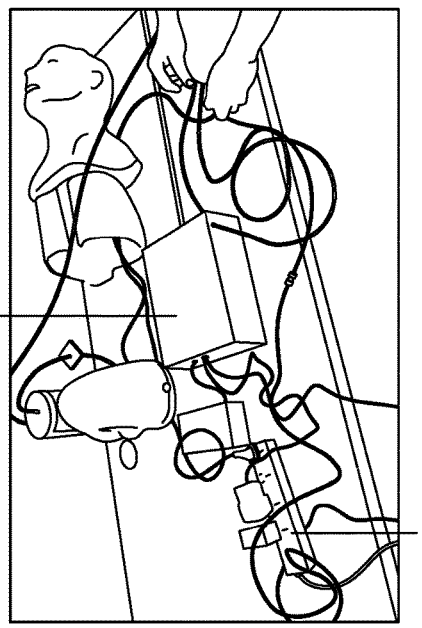
FIG. 16A is a pictorial of the closed controller, fluid lines, and secretion collection reservoir.
Figure 16C:
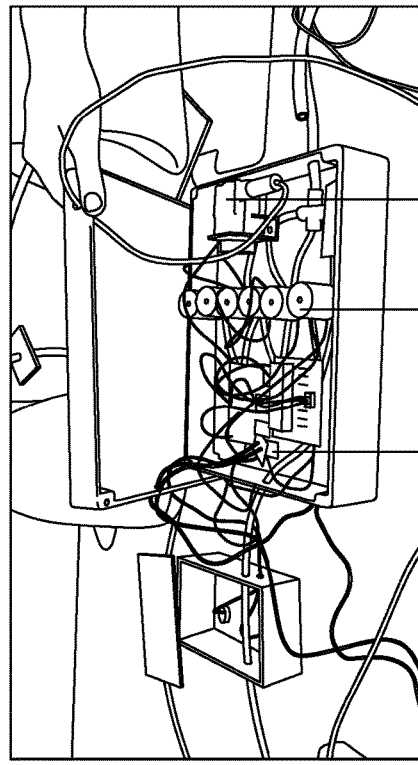
FIG. 16C is yet another close-up pictorial showing controls, controller having suction valves, pressure controller, vacuum, and fluid lines.

FIGS. 16A-16C shows pictorials of a fluid management system setup reduced to practice. FIG. 16A shows the controller in connection with various fluid lines. FIGS. 16B and 16C shows close-ups of the controller which includes valves, pump, motor, and micro-controls.

Respiratory Insertion Devices

As mentioned, the fluid management systems described above may be coupled to a respiratory insertion device. FIGS. 17-30 describe the respiratory insertion device connected to the fluid management system as well as different embodiments of the respiratory insertion device envisioned.

In some variations, a respiratory insertion device will snap over any endotracheal tube and can be slid down into the appropriate position. For example, the sheath/sleeve may be placed in the oral cavity of an intubated patient with the dorsal end reaching till the vocal chords. The sheath/sleeve may have two or more (e.g., three) parallel independent channels running with multiple openings/ports at different locations corresponding to the subglottic region, oropharyngeal region and the oral cavity. In some variations the sheath includes only two lumen (channels) as the tracheal tube onto which it is connected already has a lumen that may be used to remove fluid from a region around (and/or within) the tracheal tube. The ends of these channels having connectors for coupling with suction line tubing.

The respiratory insertion device can be constructed of any suitable materials. Such materials include but are not limited to: polyurethane, polyvinyl chloride (PVC), polyethylene terephthalate (PETP), low-density polyethylene (LDPE), polypropylene, silicone, neoprene, polytetrafluoroethylene (PTFE), or poly-isoprene or any other relevant elastomer, plastic, or rubber or any other bio-compatible material.

The respiratory insertion device may be connected to connecting tubing, and the sensing unit(s) may be placed for optimum sensing. The sensing unit contains fluid detection sensors and sends its values to a control and processing unit which has a microcontroller, and a set of valves namely, suction shut on/off valve, lavage shut on/off valve, suction pressure control valve, lavage pressure control valve. It also houses the variable output pump, collection jar and display. The collection jar has a provision to attach a sample collection system which includes but not limited to the small jar, for collection of small amount of secretions to be sent to the microbiology/pathology lab.

The control and processing unit is driven by an external or internal power supply. It takes the suction from an external negative pressure source such as any suction creating apparatus (wall mounted suction line, portable suction system, independent suction system) and is connected to the control unit.

Figure 17:
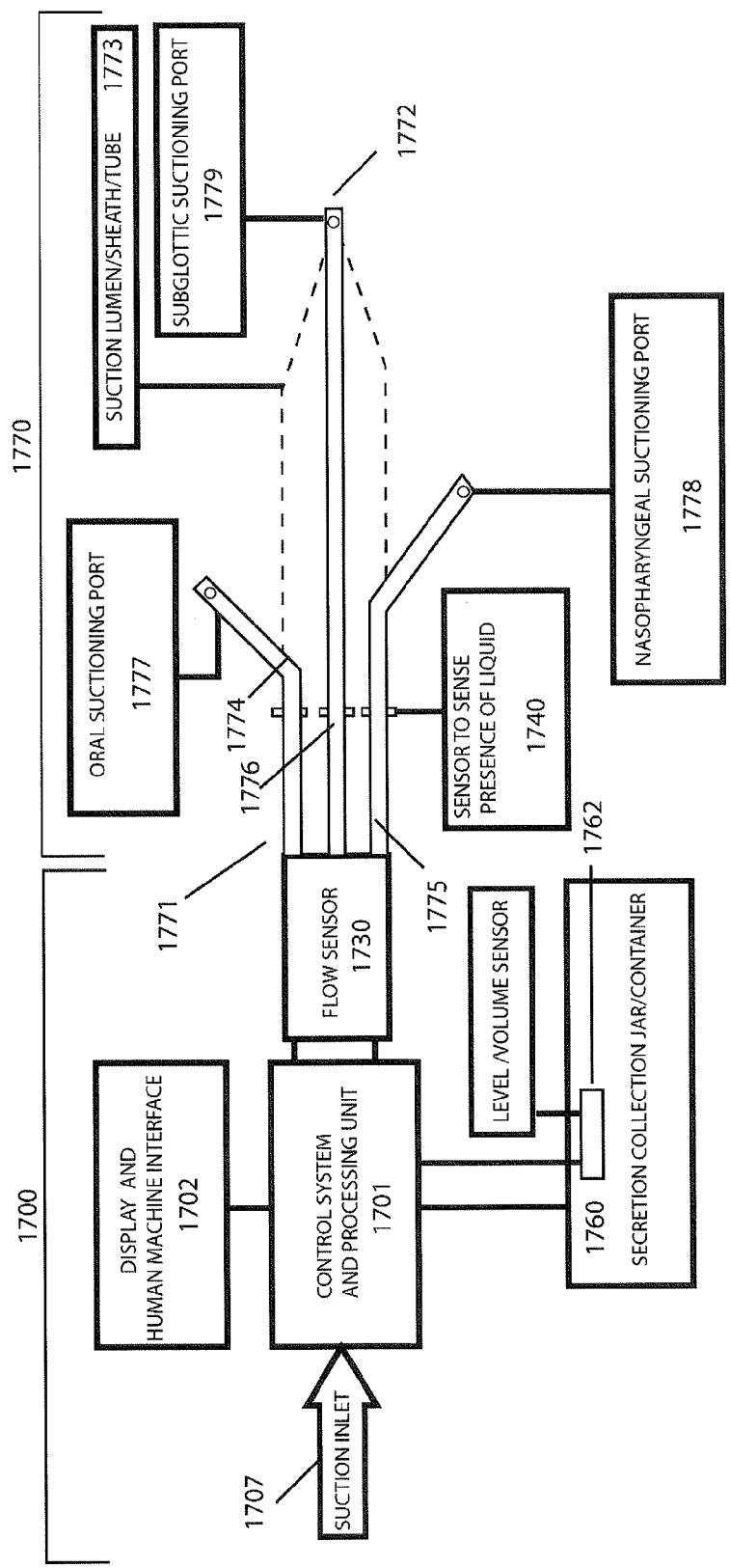
FIG. 17 illustrates another representative block diagram of the fluid management system having three independent suctioning lines.

FIG. 17 shows the global tracheal management system which includes a fluid management system 1700 and a respiratory insertion device 1770. In general respiratory insertion device 1770 includes a sheath 1773 having a proximal end 1771 and a distal end 1772. Proximal end 1771 is situated adjacent to fluid management system 1700. Distal end 1772 corresponds to the subglottic region of an intubated patient. Respiratory insertion device 1770 generally includes at least two lumen and typically comprises a third. In FIG. 17, three lumen 1774, 1776, and 1775 are shown. The proximal and distal end of each of lumen 1774, 1776, and 1775 extend longitudinally along the length of sheath 1773. Each of the proximal end of lumen 1774, 1776, and 1775 can couple to corresponding fluid lines (not shown) of fluid management system 1600. Distal ends of lumen 1774, 1776, and 1775 corresponds to different regions along a tracheal tube. In particular, the oral cavity, the oropharynx, and the subglottic regions on an intubated patient are of interest. Distal end of lumen 1774, 1776, and 1775 each include oral suctioning ports 1777, 1778, and 1779 for detection and withdrawal of fluid from these regions in direct contact with the ports. Further shown in FIG. 17 are flow sensors 1730 and liquids/pressure sensors 1740. Flow sensors 1730 can detect the flow rate of fluid with the fluid lines and aid in the regulation of flow within the fluid lines. Pressure sensors 1740 can detect the amount of resistance when negative pressure is applied through the fluid lines and relay to the controller if the amount of resistance is greater than a threshold value, indicating that there is blockage in the line. While pressure sensors 1740 shown in FIG. 17 are located on lumen 1774, 1776, and 1775, the pressure sensors can be placed on the fluid line and external to the respiratory insertion device.

Figure 18:
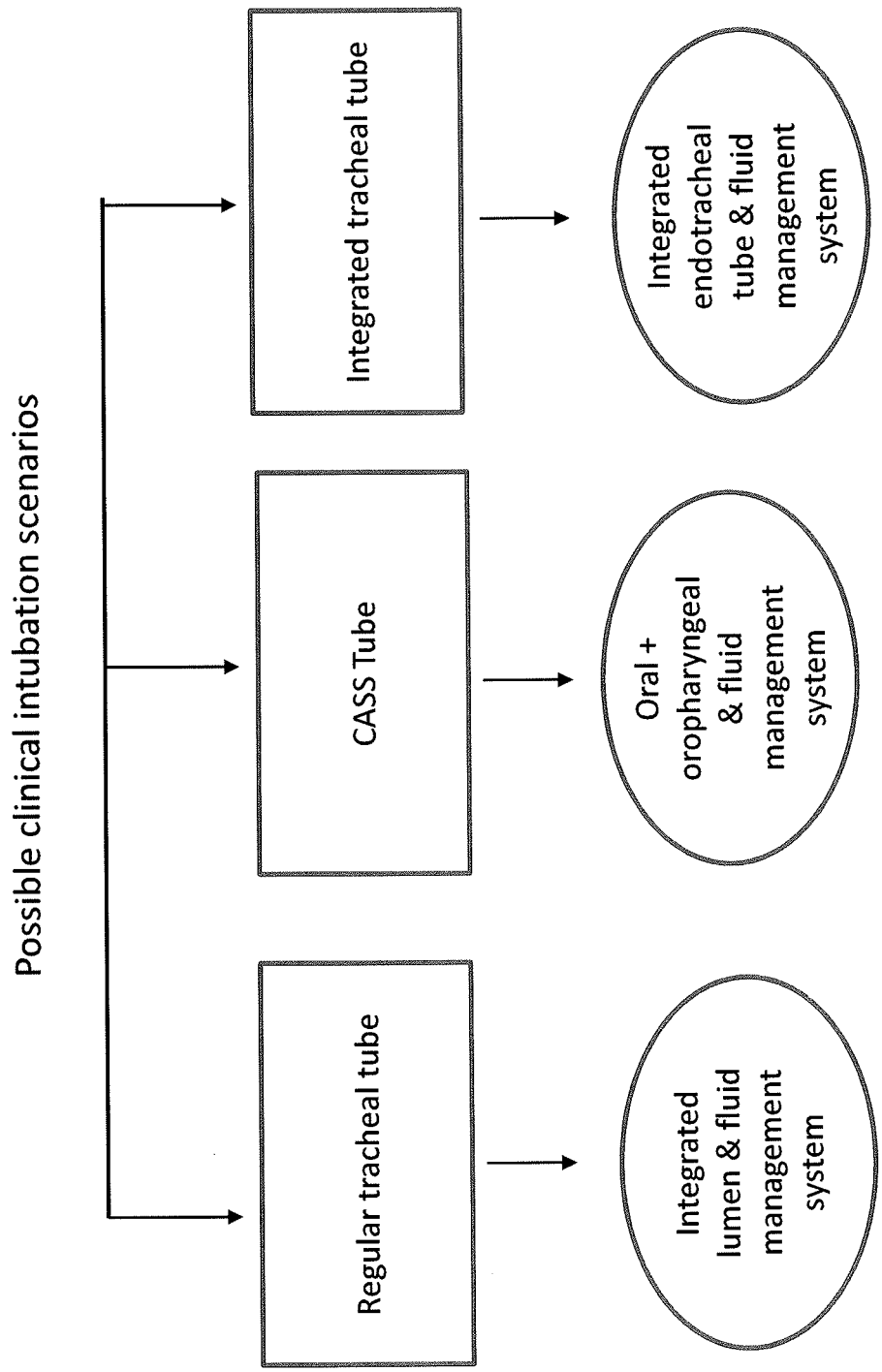
FIG. 18 illustrates various combinations of traditional tracheal tube and systems with the disclosed fluid management system and an insertion body.

Different combinations of the respiration insertion device can be coupled to the various configurations of the fluid management system discussed above. FIG. 18 shows a subset of possible combinations of respiratory insertion device with the fluid management system. First of all, the fluid management system can be used with a traditional tracheal tube, more specifically an endotracheal tube or a tracheostomy tube. This may not be ideal because traditional tracheal tube do not possess the necessary lumen and corresponding ports that would allow monitoring and evacuation of fluid. FIG. 18 also shows that the fluid management system can be used with a modified tracheal tube having lumen that attach to an existing tracheal tube. FIG. 18 also shows a continuous aspiration of subglottic secretion (CASS) tube which allow for suctioning along the subglottic regions as well as use with innovative integrated tracheal tube configurations that will also be more thoroughly discussed in the following paragraphs. And finally, the diagram indicates that the fluid management system can also work with an integrated endotracheal tube where the lumen are integrated into the device body.

Figure 19A:
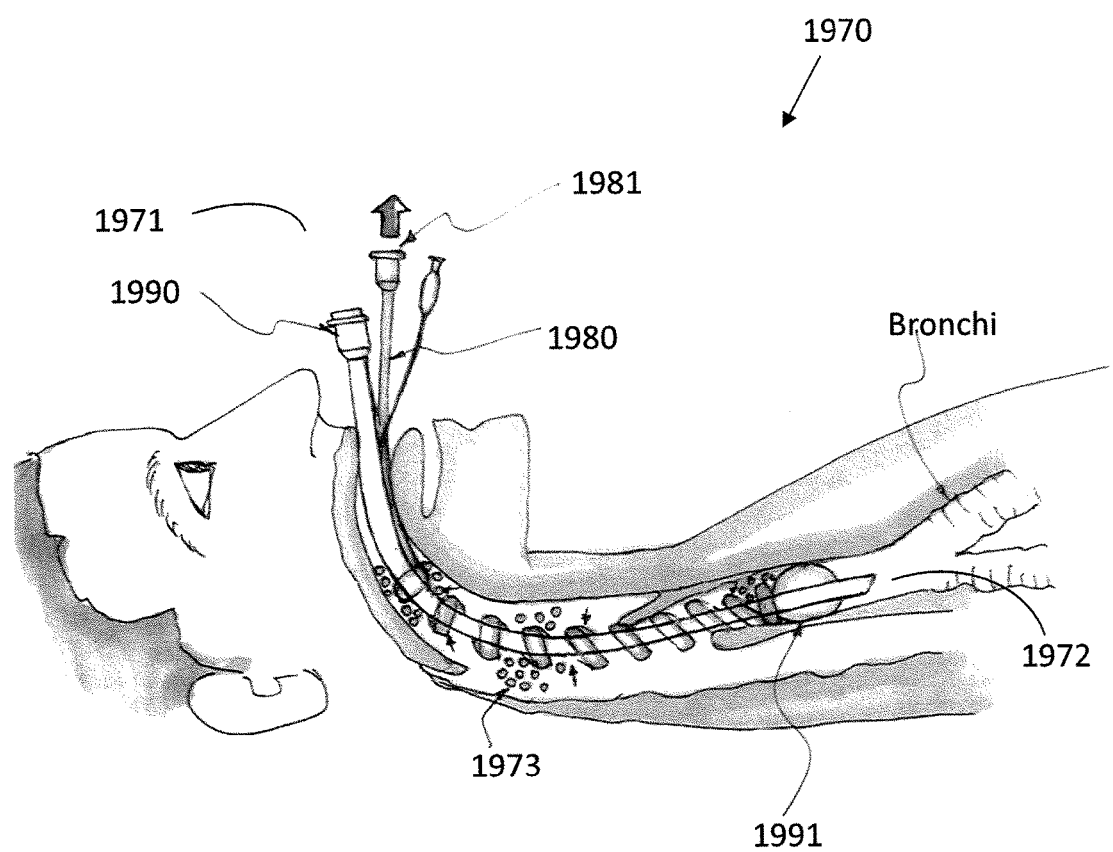
FIG. 19A shows one variation 19B illustrates a spiral embodiment of a respiratory insertion device.

FIGS. 19A-19D show a first embodiment of a respiratory insertion device 1970. Respiratory insertion device 1970 has a proximal end 1971 that is near the mouth of the intubated patient and a distal end 1972 that corresponds to the end of the patient's trachea and the top of the bronchi region. Respiratory insertion device 1970 has a spiral configuration where a device body 1973 winds around an existing tracheal tube 1990. Device 1970 is prevented from pushing past a safe region of the patient's respiratory tract once the distal end of device 1970 abuts a cuff 1991 of the tracheal tube and proper positioning of device 1970 along the existing tracheal tube is achieved when the distal end of device 1970 sits against cuff 1991 and the proximal end of device 1970 adjoins the proximal end of the existing tracheal tube. Device 1970 includes at least one device fluid line 1980 for suctioning. Device fluid line 1980 may include a coupler 1981 for attaching to the fluid lines of the fluid management system. The small circles along the tracheal tube show where fluid is most likely to accumulate. As prior references have indicated, one area of fluid accumulation corresponds to the subglottic region of the patient especially around the cuff. Other two regions not specifically mentioned and targeted by earlier tracheal tube fluid management devices are the oral cavity and the oropharyngeal regions adjacent to the tracheal tube. An unconscious intubated patient cannot tell that saliva is pooling in their mouth and has no automatic reflex to rid his or her mouth of the fluid especially with the presence of the tracheal tube. The oropharyngeal region is also susceptible to fluid accumulation due to the arcuate bend in the tracheal tube as it passes the oral cavity into the trachea in combination with the typical horizontal position of an intubated patient. FIG. 19A shows a respiratory insertion device similar to that in FIG. 17; FIGS. 19B, 19C, and 19D show enlarged views of portions of this device. Suctioning ports are disposed at various regions on the device body 1973. A blow-up view that corresponds to the oropharyngeal region along the tracheal tube shows a plurality of ports 1978. The circles and arrows show the fluid and other debris moving toward ports 1978 to be suctioned away. While not specifically shown, ports are also disposed on the respiratory insertion device body that corresponds to the oral cavity and the subglottic region of the intubated patient. Also, the spacing of the ports corresponding to different regions of the tracheal tube should be at least 0.4 inches from each other (e.g., the ports at the distal ends of the lumen). At the proximal ends of the lumen, which may connect to fluid lines, ports into the lumen may be immediately adjacent to each other or may extend as tubes from the device. This requirement does not apply to ports associated with the same region, which is shown in the enlarged views in FIGS. 19B, 19C, and 19D.

Figure 20:
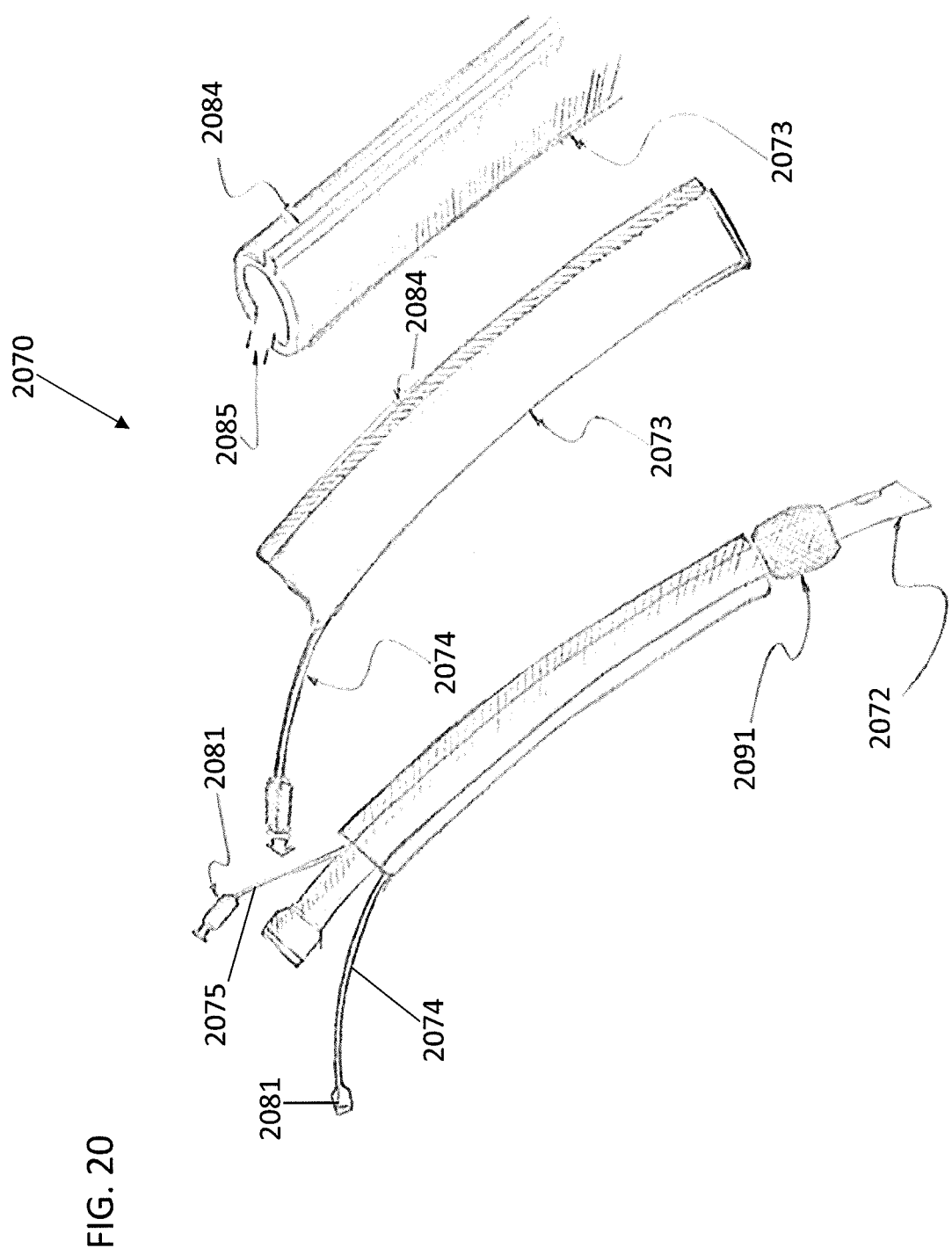
FIG. 20 illustrates a hinged embodiment of the respiratory insertion device.

FIG. 20 illustrates aspects of a respiratory insertion device 2070 for removing fluid from two or more regions along a tracheal tube in accordance with some embodiments. Device 2070 includes a sheath 2073. Sheath 2073 having a hinge 2084 and an opening 2085. Disposed along the perimeter of sheath 2073 are a plurality of lumen. In FIG. 20, two lumen 2074 and 2075 are shown. Lumen 2074 and 2075, when connected to fluid lines of the fluid management system, are able to suction two different locations of an existing tracheal tube through ports (not shown) disposed adjacent to the distal end 2072 of device 2070. In use, hinge 2084 of sheath 2073 can open and increase the circumference of opening 2085. A user can then more easily slide device 2070 over an existing tracheal tube either prior to placing the tracheal tube in a patient or after placement of the tracheal tube. Couplers 2081 are also present for connecting to the fluid management system. In variations of this embodiment, more than two lumen are disposed along the perimeter of the device sheath.

Figure 21:
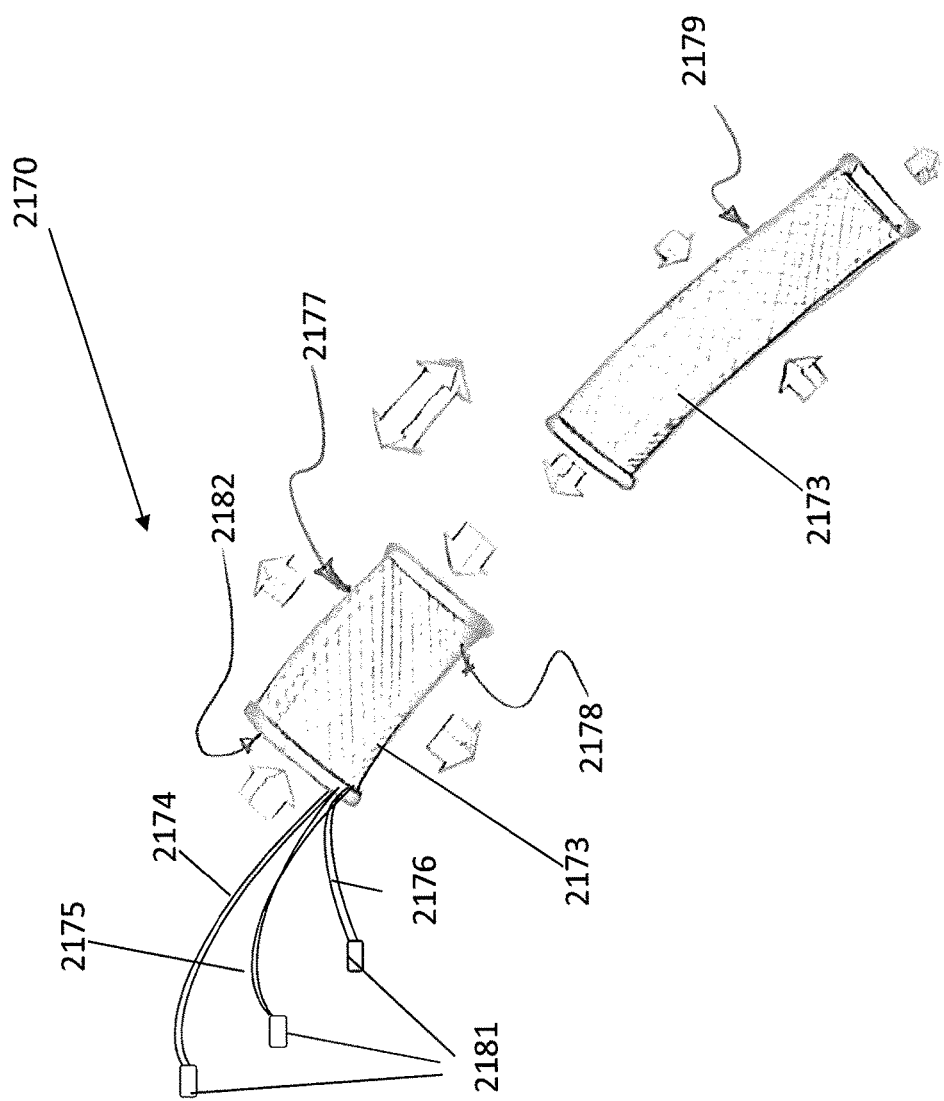
FIG. 21 illustrates a stent-like embodiment of the respiratory insertion device.

FIG. 21 illustrates aspects of a respiratory insertion device 2170 for removing fluid from two or more regions along a tracheal tube in accordance with some embodiments. Device 2170 includes one or more sleeve 2173. Sleeve 2173 function much like a stent wherein sleeve 2173 expands laterally when a force is longitudinally applied and thus device 2170 can be segmentally inserted over an existing tracheal tube. Device 2170 may include lumens along the perimeter of the top sleeve that extend along the longitudinal axis of the top sleeve. The top sleeve may include a lumen that terminates at a top sleeve port opening for suctioning a first region along the existing tracheal tube. The first region may correspond to the oral cavity of the intubated patient. Lumen 2174, 2175, and 2176 are shown entering the sleeve 2173 at a ring 2182. The top sleeve can align and couple to lower sleeves having corresponding lumen that terminate at port openings along the length of the lower sleeve. A first port opening 2177 may correspond to the oral cavity of a patient. Other port openings 2178 and 2179 may correspond to a second and a third region along the existing tracheal tube such as the oropharyngeal and subglottic regions. While the lumen in FIG. 21 are all shown to insert at largely one point onto the sleeve, it is also possible for the different lumen to insert at different points on the ring and having corresponding channels in the lower sleeves. Also, each lumen include couplers 2181 for attaching to the fluid management system or the like. It should be note that in positioning this device embodiment, ventilation may have to be disrupted for a short period to enable fitting of the sleeve over the existing tracheal tube.

FIGS. 22A-22C illustrate aspects of a respiratory insertion device 2270 for removing fluid from two or more regions along a tracheal tube in accordance with some embodiments. Device 2270 is designed to fit over an existing tracheal tube and includes a series of stacked rings 2282 held together by a series of support structures 2273. Stacked rings 2282 may include at least one set of longitudinally-aligned ring apertures. Device 2270 further include an integrated lumen 2281 that is able to reach various points along the length of the existing tracheal tube. The distal end of the integrated lumen 2281 includes a series of tentacle-like lumen that thread through at least one of the longitudinally-aligned ring apertures 2288. The tentacle-like lumen at the distal end that are able to reach farther along the existing tracheal tube may thread through two or more of the longitudinally-aligned ring apertures 2288. The tentacle-like lumen 2274, 2275, and 2276 terminate with corresponding suctioning ports 2277, 2278, and 2279 that are able to remove fluid from the corresponding regions along the existing tracheal tube. Finally, the lumen come together at the proximal end of the integrated lumen 2281 and couple to a connector 2281 that links the lumen to the fluid management system.

Figure 23B:
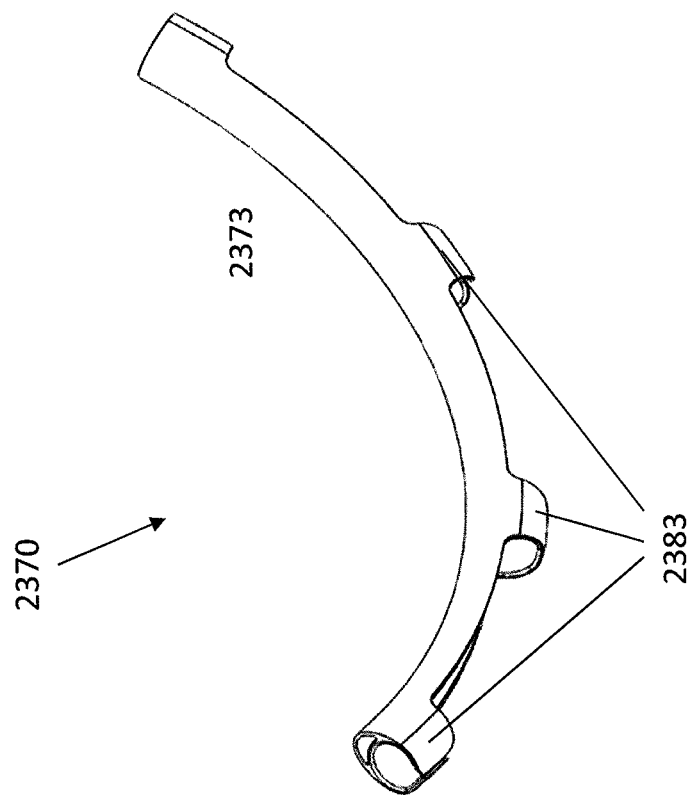
FIG. 23B illustrates a side view of the alternative embodiment of the clip respiratory insertion device of FIG. 23A.
Figure 23A:
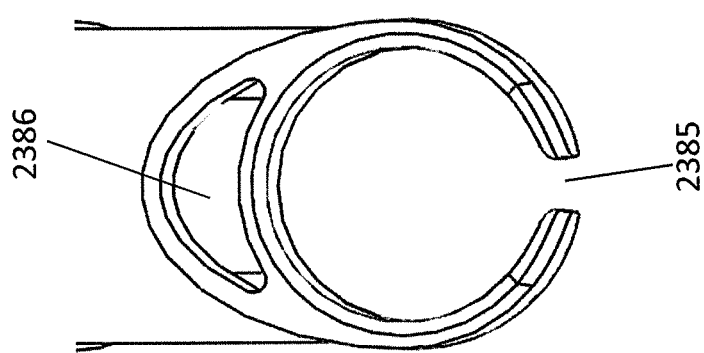
FIG. 23A illustrates a front view of an alternative embodiment of a clip respiratory insertion device.

FIGS. 23A-23B illustrate aspects of a respiratory insertion device 2370 for removing fluid from two or more regions along a tracheal tube in accordance with some embodiments. Device 2370 is able to attach to an existing tracheal tube. Device 2370 includes a device body 2373 along one side and a series of clips 2383 that enables device 2370 to attach to the existing tracheal tube. Series of clips 2383 each include an opening 2385 that allows a user to slightly increase the diameter of the series of clips 2383 for fitting device 2370 over the existing tracheal tube. Device 2370 includes a cavity 2386 that runs essentially the entire length of device 2370. While not shown, catheter or tubing can be inserted through cavity 2386 to terminate at various points along device 2370 for suctioning at different regions along the tracheal tube.

An alternative embodiment to device 2370 is a device 2470 as shown in FIGS. 24A-24B. One difference between device 2470 and 2370 is that device 2470 is composed of two different materials. The majority of device 2470 is composed of a softer elastomer that is flexible along the longitudinal axis of the device. Device 2470 includes regions having "C" shaped-supports 2487 comprising stiffer material. The C-shaped supports 2487 are situated along the longitudinal axis of device 2470 provides overall rigidity in the transverse plane of device 2470. Device 2470 includes a channel 2486 that runs along and follows the curve of the device body. Channel 2486 may retain at least one catheter or tubing body for suctioning at least one area along the existing tracheal tube. Where there are greater than one catheter or tubing body held within channel 2486, the distal ends of the catheter or tubing body terminates at different points along the existing tracheal tube.

Figure 25B:
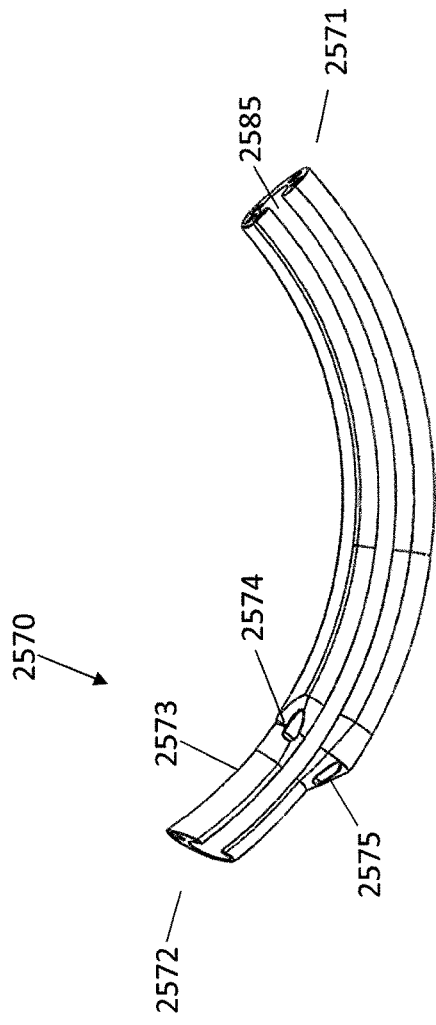
FIG. 25B is a side view of an embodiment of the respiratory insertion device having five channels for lavage and secretion removal.
Figure 25C:
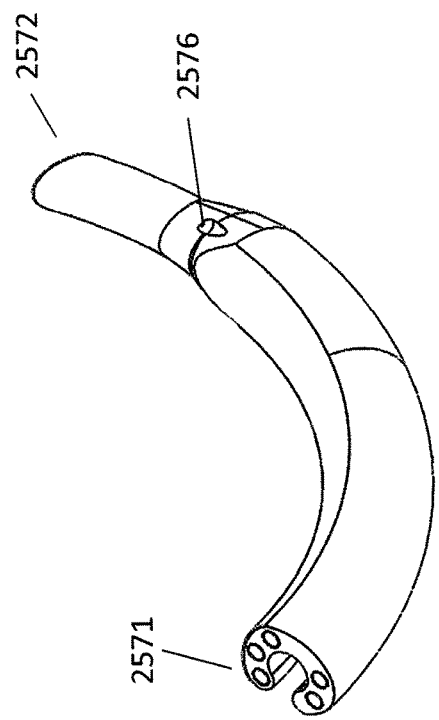
FIG. 25C is a perspective view of an embodiment of the respiratory insertion device having five channels for lavage and secretion removal.
Figure 25A:
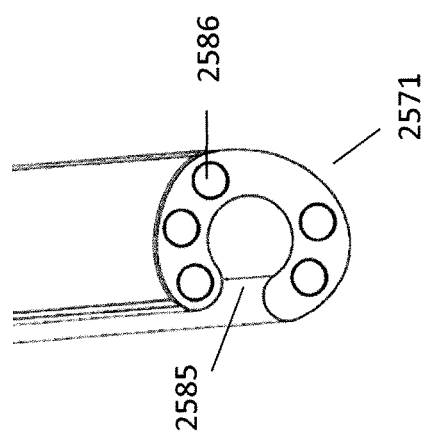
FIG. 25A is a front perspective view of an embodiment of a respiratory insertion device having five channels for lavage and secretion removal.

Next, FIGS. 25A-25C illustrate aspects of a respiratory insertion device 2570 for removing fluid from two or more regions along a tracheal tube in accordance with some embodiments. Device 2570 is a variation on the clip format. Device 2570 has a proximal end 2571, a distal end 2572, and a device body 2573. Proximal end 2571 is situated near a patient's mouth, while distal end 2572 is located between the lower trachea and bronchi of a patient. FIG. 25A shows a close-up of proximal end 2571 which includes a series of channels 2586 that follow the length of device body 2573 and terminate at various points along an existing tracheal tube. In some examples, channels 2586 correspond to the oral, oropharyngeal, and subglottic regions on a patient. FIGS. 25B and 25C show that some of the channels 2586 terminate at three ports 2574, 2575, and 2576 for suctioning different regions along the existing tracheal tube. Depending on how fluid lines are attached, some of the channels can be used for lavage of various regions of the patient's oral, oropharyngeal, and subglottic cavities. Finally, device 2570 includes an opening 2585 that allows for easier placement of device 2570 over a tracheal tube.

FIGS. 26A-26C shows a variation of the device shown in FIGS. 25A-25C. Similarly, device 2670 has a clip-on format that allows it to attach to an existing tracheal tube. Device 2670 includes a device body 2673, a proximal end 2671, and a distal end 2672. Device 2670 also has a C-shaped cross section having an opening 2685, where the distance of the opening is greater than that for device 2570. At proximal end 2671 of device 2670 includes two couplers 2681 that allows device 2670 to connect to a suctioning system such as the fluid management system described earlier. Couplers 2681 attach to channels 2674 and 2675 that run along the length of device 2670 and terminates at different zones along device 2670. At the terminus of channels 2674 and 2675 are ports 2674 and 2675 for suctioning different regions along an existing tracheal tube.

FIGS. 27A-27D illustrate aspects of a respiratory insertion device 2770 for removing fluid from two or more regions along a tracheal tube in accordance with some embodiments. Device 2770 is another version of a clip-on fluid suctioning device that can be mated with an existing tracheal tube. Device 2770 has a device body 2773, a proximal end 2771 that is close to a patient's oral cavity when in use, and a distal end 2772 that is between the patient's lower trachea and bronchi when in use. Device 2770 includes a series of clips 2783 for coupling to a tracheal tube. Device 2770 also includes stacked lumen 2774, 2775, and 2776 that run the length of device body 2773 and terminate at different regions along device body 2773. At the terminus of lumen 2774, 2775, and 2776 are corresponding ports 2777, 2778, and 2779 for working with the fluid management systems described above or other like systems to detect and suction fluid from different regions along the tracheal tube. While not shown, proximal end of lumen 2774, 2775, and 2776 can be coupled to fluid lines of the fluid management system or other like systems.

Figure 28F:
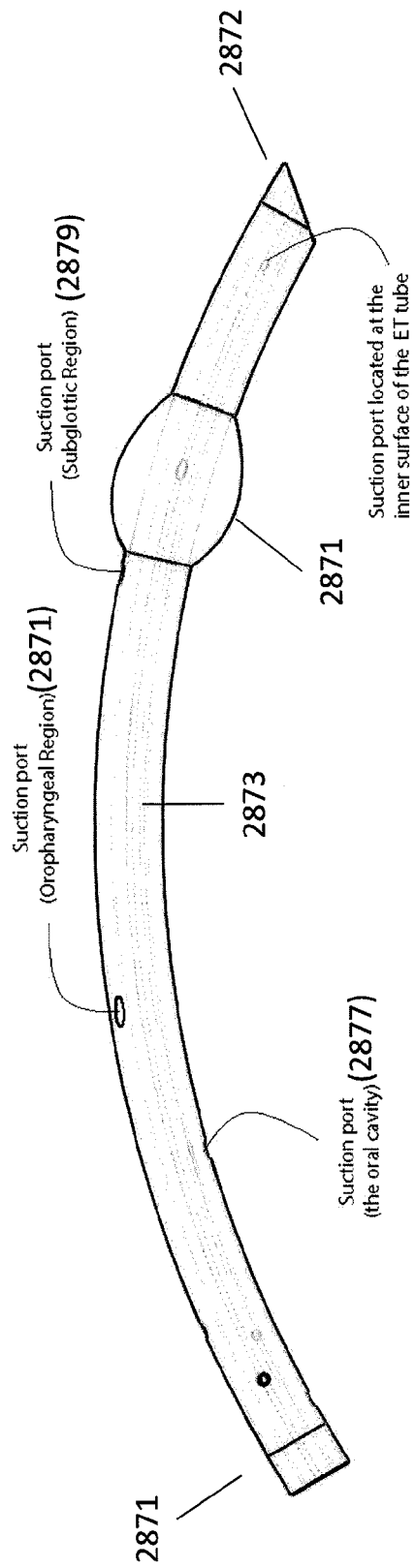
FIG. 28F shows another view of the respiratory insertion body having three ports along its main body.
Figure 28G:
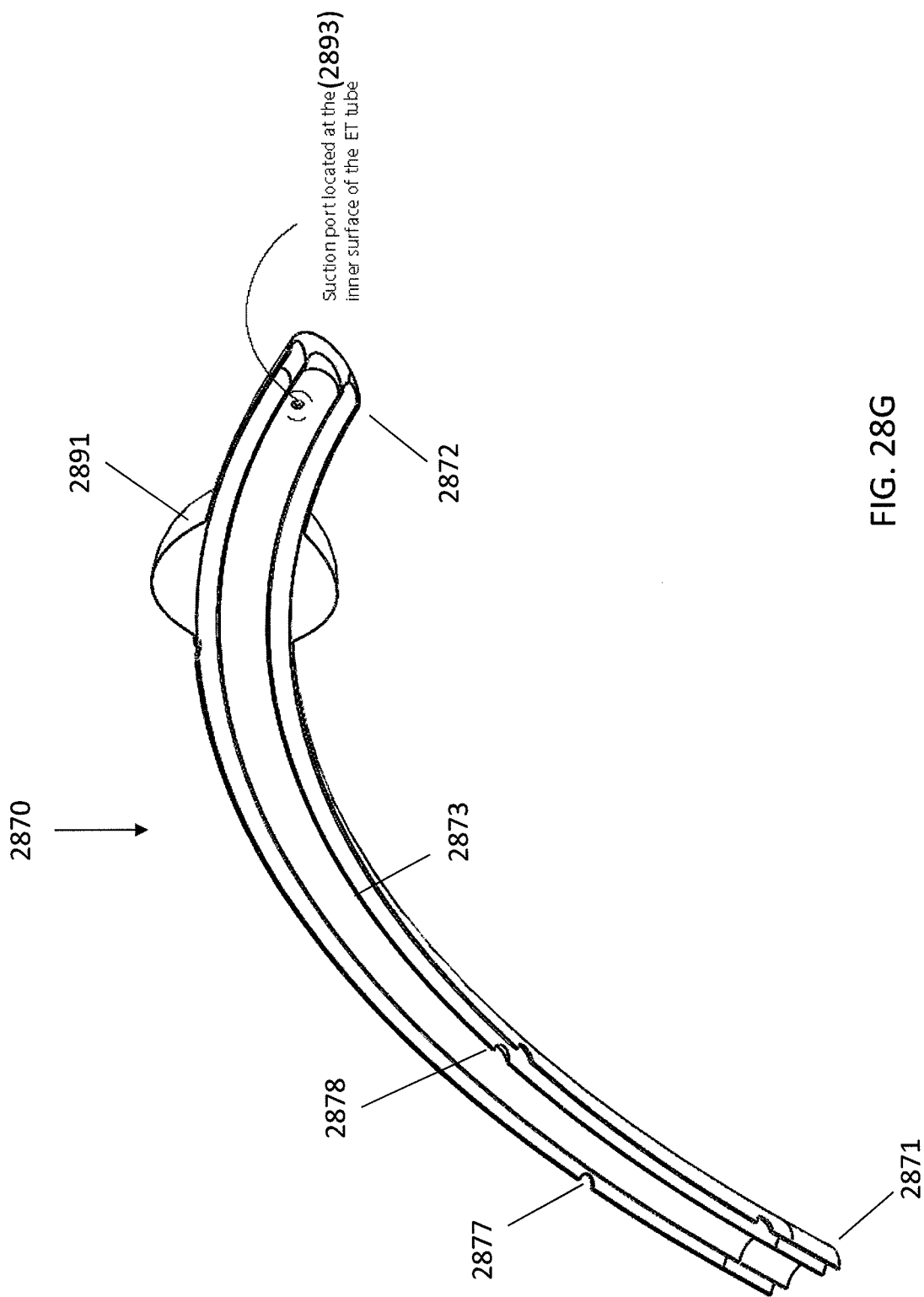
FIG. 28G shows a cross-section of the respiratory insertion body of FIGS. 28A-28F, where an internal port for suctioning the inside of the endotracheal tube is shown.

FIGS. 28A-28G illustrate aspects of a respiratory insertion device 2870 for removing fluid from two or more regions along a tracheal tube in accordance with some embodiments. Device 2870 is an integrated tracheal tube having sensing and suctioning capabilities as well as an airway passage for connecting to an external breathing mechanism. Device 2870 includes a device body 2873, a proximal end 2871, and a distal end 2872. A cuff 2891 is located towards distal end 2872 of device 2870. Device 2870 further includes a tracheal tube portion 2890, a cuff inflation line 2892, and a first, second, and third lumen 2874, 2875, 2876 for suctioning different regions along the respiratory tract of a patient. The distal ends of lumen 2874, 2875, and 2876 all terminate with corresponding ports 2877, 2878, and 2879 that aid in sensing and removing fluid from different points along device body 2873. FIG. 28G shows a cross-section of this particular embodiment of respiration insertion device 2870 where respiration insertion device 2870 further includes an internal port 2893 for suctioning in internal region of the tracheal tube portion of respiration insertion device 2870. Also visible are the channels associated with ports 2877 and 2878 which correspond to the oral cavity and the oropharyngeal cavity regions.

Figure 29B:
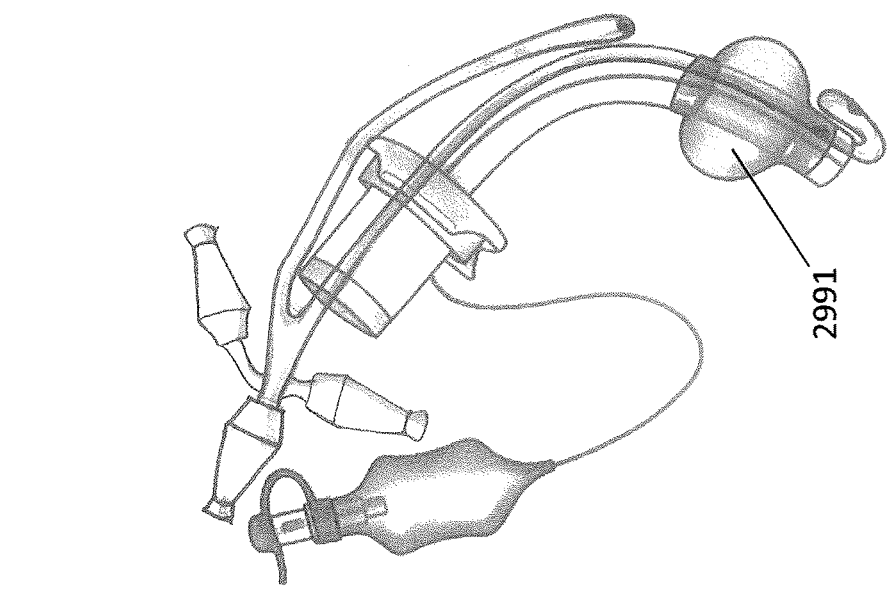
FIG. 29B shows the respiratory insertion device of FIG. 29A engaged with a tracheostomy tube.
Figure 29A:
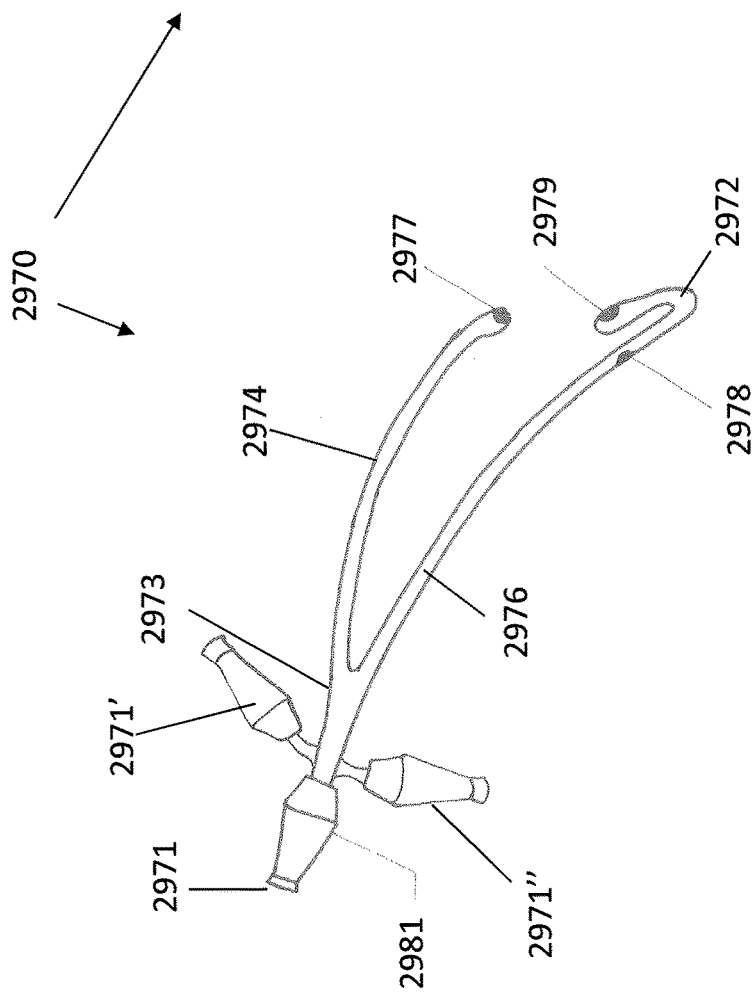
FIG. 29A is a drawing of a first embodiment of a respiratory insertion device for use with a tracheostomy tube.
Figure 30:
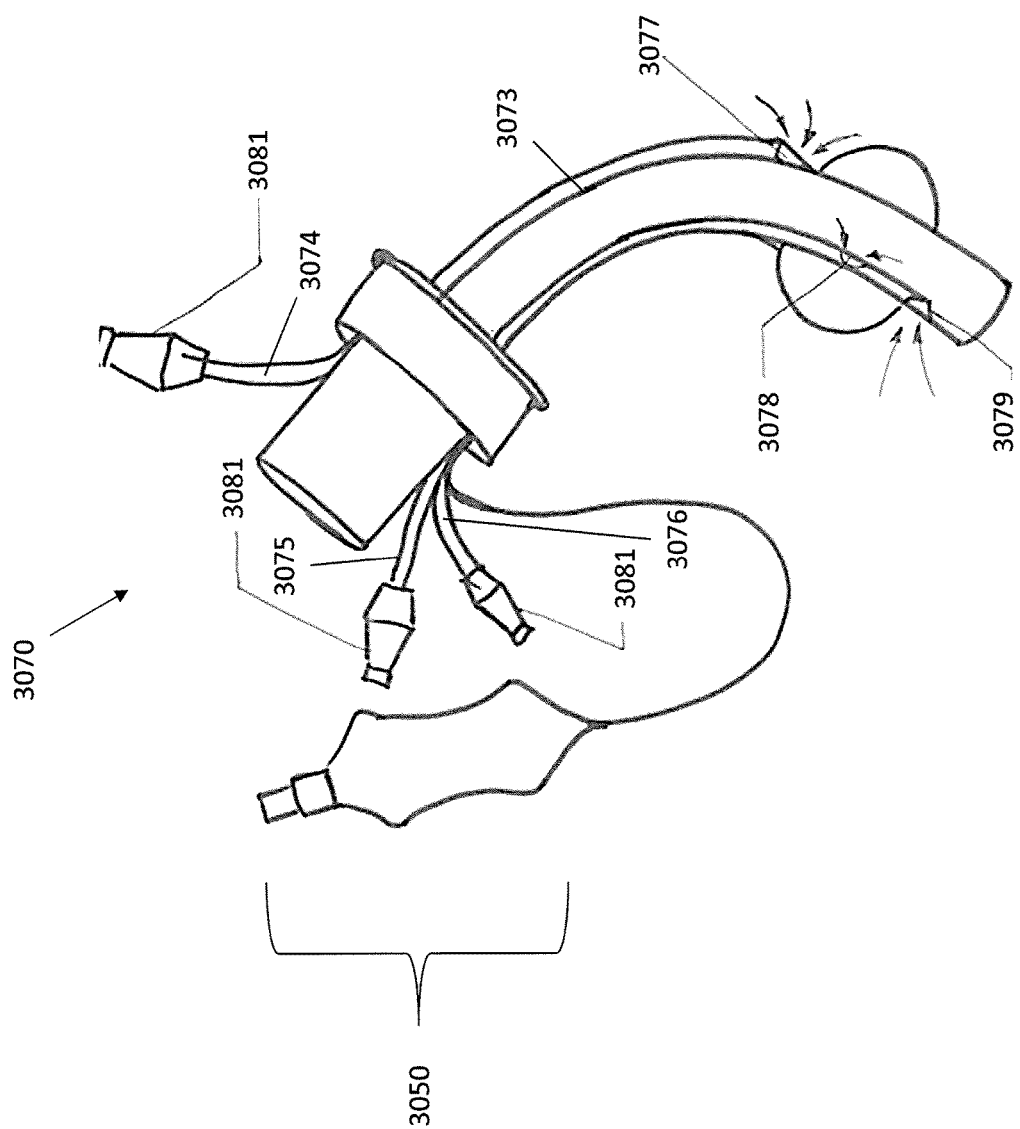
FIG. 30 is an example of an integrated respiratory insertion device with the tracheostomy tube.

Turning to FIGS. 29A-30, devices for use in a tracheostomy scenario will be described. FIGS. 29A and 29B show a first embodiment of a tracheostomy device 2970. Device 2970 includes a proximal end with one or more (e.g., three in this example) fluid line connectors 2971, 2971', 2971", a distal end 2972, and a device body 2973. Device body 2973 is bifurcated into a first and second lumen, 2974 and 2976. In use, first lumen 2974 is located outside of the tracheostomy tube while second lumen 2976 is largely situated within the tracheostomy tube as shown in FIG. 29B. First lumen 2974 includes a first port 2977 at its terminus that is used for detecting and removing fluid from a first external surface of the tracheostomy tube, primarily above an inflatable cuff 2991 of the tracheostomy tube. Second lumen 2976 is longer than first lumen 2974 and includes a bend at its terminus. At the bend, second lumen 2976 exits the tracheostomy tube and terminates below cuff 2991. At its terminus, second lumen 2976 includes a second port 2979 for sensing and suctioning a lower region of the tracheostomy tube just below cuff 2991. Second lumen 2976 also includes a third port 2978 that is situated within and near the distal end of tracheostomy tube for sensing and removing fluid from the lower portion of the tracheostomy tube. Finally, device 2970 includes a coupler 2981 for attaching to the fluid management or like system for sensing and removing fluid from different regions along the tracheostomy tube.

A second embodiment of a tracheostomy device 3070 is shown in FIG. 30. Device 3070 is an integrated tracheostomy tube and a fluid sensing and management device. Device 3070 includes three independent lumen 3074, 3075, and 3076 that is integrated with a tracheostomy tube 3073. The proximal ends of lumen 3074, 3075, and 3076 include couplers 3081 for connecting to the fluid management or other like systems. The terminus of each lumen 3074, 3075, and 3076 are at different locations along tracheostomy tube 3073. At the terminus of each lumen 3074, 3075, and 3076 are corresponding ports 3077, 3078, and 3079 for sensing and removing fluid from their corresponding regions. In some instances, fluid, such as a lavage fluid 3050 can be introduced into the interior of tracheostomy tube 3073 and the rinse fluid can be removed via ports 3077, 3078, and 3079.

Method of Using the Fluid Management System with the Respiratory Insertion Devices The following paragraphs describe the method of using the fluid management system and with the respiration insertion device. A user can insert a respiratory insertion device having a plurality of openings into a subject's respiratory tract so that a first opening is positioned at oral cavity (e.g., near a base of the subject's tongue), a second opening is positioned at the subject's oropharynx, and a third opening is positioned at the subject's subglottic region. In one case, the respiratory insertion body attaches to a pre-existing tracheal tube, while in other cases, the respiratory insertion body incorporating a tracheal tube, is newly inserted into a patient's trachea.

Next, the user coupling the respiratory insertion body to a controller by connecting a first lumen of the respiratory insertion body that is in communication with the first opening to a first fluid line, connecting a second lumen of the respiratory insertion body that is in communication with the second opening to a second fluid line, and connecting a third lumen of the respiratory insertion body that is in communication with the third opening to a third fluid line. The operator then can set the controller to automatically, at a predetermined time period, apply suction through each of the first, second and third fluid lines, and automatically turn off suction in one or the first, second or third fluid lines when fluid flow through one of the fluid lines falls below a flow threshold and when pressure in that fluid line is above a pressure threshold, and applying positive pressure in that fluid line to clear a blockage when fluid flow through that fluid line falls below the flow threshold and when pressure is below the pressure threshold. The operator can also choose to engage a lavage liquid to various regions along the tracheal tube.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for automatically removing fluid from multiple regions of a respiratory tract and lavaging an oral cavity portion of the respiratory tract, the system comprising:
   a controller comprising controller circuitry and one or more valves configured to couple to a source of air pressure;
   a plurality of fluid lines, wherein the fluid lines couple with the one or more valves of the controller, and wherein the controller circuitry is configured to control the one or more valves to apply positive or negative pressure through each fluid line of the plurality of fluid lines;
   a plurality of flow sensors and pressure sensors, wherein the fluid lines are each coupled to a flow sensor and a pressure sensor that are configured to report fluid flow and pressure within the fluid line to the controller;
   a source of lavage liquid, wherein the controller is configured to apply positive pressure to deliver lavage liquid; and
   a plurality of collection containers each coupled to a fluid line of the plurality of fluid lines and configured to collect fluid from the fluid lines, wherein the plurality of collection containers are connected between a pressure control of the controller and the plurality of flow sensors;
   wherein the controller circuitry is configured to periodically, automatically, and independently apply negative pressure to each of the fluid lines, to continue applying negative pressure until there is no more flow and to stop applying negative pressure in each fluid line of the plurality of fluid lines when the fluid flow in that fluid line indicates an absence of secretions, and to detect a blockage in the fluid line based on fluid flow and pressure in that fluid line;
   further wherein the controller circuitry is configured to clear a block in that fluid line.

2. The system of claim 1, further comprising an input configured to receive user-selected control information comprising one or more of: lavage delivery frequency, lavage duration, lavage pressure, suction application frequency, and suction pressure.

3. The system of claim 1, wherein the controller further comprises a display, and wherein the controller circuitry is configured to display for one or more of the first, second and third fluid lines data comprising one or more of: flow rate of a secretion within the fluid line, thickness of secretion within the fluid line, volume of secretion within the fluid line, or color of the secretion within the fluid line.

4. The system of claim 1, wherein the controller is configured to apply positive pressure to deliver the lavage fluid through one of the fluid lines and to apply negative pressure to one or more other of the fluid lines to remove the lavage fluid.

5. The system of claim 1, wherein the plurality of fluid lines comprises a first, second and third fluid lines and wherein the controller circuitry is configured to independently apply negative pressure through each of the first, second and third fluid lines.

6. The system of claim 1, wherein the plurality of fluid lines comprises a first, second, third and fourth fluid lines and wherein the controller circuitry is configured to independently apply negative pressure through each of the first, second, third and fourth fluid lines.

7. The system of claim 1, wherein the plurality of fluid lines comprises one or more lavage delivery fluid lines that are connected to the source of lavage liquid and wherein the controller is configured to apply positive pressure to the one or more lavage delivery fluid lines to deliver lavage fluid.

8. The system of claim 1, further comprising a pump configured to apply positive pressure, wherein the pump is in communication with the controller and the source of lavage fluid.

9. The system of claim 1, wherein the source of lavage liquid comprises a receptacle configured to hold a lavage liquid.

10. The system of claim 1, wherein the one or more valves comprises a plurality of suction valves, wherein each of the fluid lines of the plurality of fluid lines is in communication with a suction valve of the plurality of suction valves.

11. The system of claim 1, wherein the plurality of flow sensors are outside of the plurality of fluid lines.

12. The system of claim 1, wherein the controller circuitry is configured to apply positive pressure to deliver lavage fluid through one or more of the plurality of fluid lines.

13. The system of claim 1, wherein the controller circuitry is configured to periodically apply positive pressure to deliver lavage fluid through one or more of the plurality of fluid lines at a lavage delivery frequency.

14. The system of claim 1, wherein the collection containers are connected to the fluid lines between the one or more valves and the source of air pressure.

* * * * *